(12) United States Patent
Auner et al.

(10) Patent No.: US 6,848,295 B2
(45) Date of Patent: Feb. 1, 2005

(54) ACOUSTIC WAVE SENSOR APPARATUS, METHOD AND SYSTEM USING WIDE BANDGAP MATERIALS

(75) Inventors: Gregory W. Auner, Livonia, MI (US); Feng Zhong, Windsor (CA); Chantelle Hughes, Troy, MI (US); Gina Shreve, Ann Anbor, MI (US); Hao Ying, Novi, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 10/125,031

(22) Filed: Apr. 17, 2002

(65) Prior Publication Data

US 2003/0196477 A1 Oct. 23, 2003

(51) Int. Cl.⁷ .......................... G01N 29/02; H02N 2/04
(52) U.S. Cl. ................. 73/24.06; 73/24.01; 310/313 R
(58) Field of Search ........................... 73/24.01, 24.06, 73/24.03, 24.04, 24.05; 310/313 R, 313 A–313 D

(56) References Cited

U.S. PATENT DOCUMENTS

| | | | |
|---|---|---|---|
| 4,189,516 A | * | 2/1980 | Dryburgh et al. ........... 428/409 |
| 4,265,124 A | * | 5/1981 | Lim et al. ..................... 73/703 |
| 4,511,816 A | | 4/1985 | Mikoshiba et al. |
| 4,937,454 A | | 6/1990 | Itoh et al. |
| 5,155,364 A | | 10/1992 | Fujii |
| 5,229,569 A | | 7/1993 | Miyauchi et al. |
| 5,343,107 A | | 8/1994 | Shikata et al. |
| 5,354,980 A | | 10/1994 | Rappoport et al. |
| 5,385,862 A | | 1/1995 | Moustakas |
| 5,456,797 A | | 10/1995 | Weber et al. |
| 5,464,984 A | | 11/1995 | Cox et al. |
| 5,510,481 A | * | 4/1996 | Bednarski et al. .......... 536/120 |
| 5,677,538 A | | 10/1997 | Moustakas et al. |
| 5,936,247 A | | 8/1999 | Lange et al. |
| 5,992,215 A | * | 11/1999 | Caron et al. ................ 73/24.01 |
| 6,084,503 A | * | 7/2000 | Ruile et al. ................. 340/10.1 |
| 6,137,231 A | | 10/2000 | Anders et al. |
| 6,144,332 A | * | 11/2000 | Reindl et al. .................. 342/42 |
| 6,243,517 B1 | | 6/2001 | Deacon |
| 6,282,357 B1 | * | 8/2001 | Kadota et al. .............. 385/129 |
| 6,312,568 B2 | * | 11/2001 | Wilke et al. ........... 204/192.18 |
| 6,450,008 B1 | * | 9/2002 | Sunshine et al. .......... 73/23.34 |
| 6,501,107 B1 | | 12/2002 | Sinclair et al. |
| 6,518,637 B1 | * | 2/2003 | Thompson et al. ......... 257/416 |
| 6,567,753 B2 | * | 5/2003 | Potyrailo ..................... 702/39 |
| 2001/0054305 A1 | * | 12/2001 | Banda et al. ............... 73/24.01 |
| 2002/0008191 A1 | | 1/2002 | Faska et al. |
| 2003/0052701 A1 | | 3/2003 | Brown et al. |

OTHER PUBLICATIONS

Baer, R. L. et al. "STW Chemical Sensors", Proc. IEEE Ultrasonic Symp., 293–298, 1992 no month.*
Zhao, Qiang et al. "Development of Wide Bandgap Semiconductor Photonic Device Structures by Excimer Laser Micromachining", 1999 Fall MRS Meeting, Nov. 1999, article W11.69., pp. 1–6.*
Krupitskaya, Regina Y. et al. "Optical Characterization of AIN Films Grown by Plasma Source Molecular Beam Epitaxy", J. Applied Phys., vol. 84, No. 5, pp. 2861–2865.*
Kaya, K. et al., "Synthesis of AIN Thin Films on Sapphire Substrates by Chemical Vapor Deposition of AIC13–NH3 Sustems and Surface Acoustic Wave Properties", Japan J. Applied Phys. vol. 35, 2782–2787, May 1996.*

(List continued on next page.)

*Primary Examiner*—Michael Cygan
(74) *Attorney, Agent, or Firm*—Kenyon & Kenyon

(57) ABSTRACT

An acoustic wave sensor to detect an analyte, the sensor comprising a piezoelectric material including a wide bandgap semiconductor material grown using plasma source molecular beam epitaxy.

10 Claims, 29 Drawing Sheets

OTHER PUBLICATIONS

Tom–Moy, May et al. "Atrazine Measurements Using Surface Transverse Wave Devices", Anal. Chem. May 1995, vol. 67, 1510–1516.*

Caliendo, C. et al. "Piezoelectric AlN Film for SAW Device Applications", Proc IEEE Ultrasonic Symp., 249–252, 1992 no month.*

Carliotti, G. et al. "The Elastic Constants of Sputtered AlN Films", Proc IEEE Ultrasonic Symp., 353–356, 1992 no month.*

Thompson, D. F. et al "Surface Transverse Wave Propogation Under Metal Strip Gratings", Proc IEEE Ultrasonic Symp., Nov. 1986, 261–265.*

Auner, G. W. "Characterization of Aluminum Nitride Thin Films Grown by Plasma Source Molecular Beam Epitaxy", SPIE vol. 248, 362–369, Oct. 1994.*

D.S. Ballantine et al, "Acoustic Wave Sensor—Theory, Design, and Physico–Chemical Applications", *Academic Press* (1997).

C. Caliendo et al, "Piezoelectric AlN Film for SAW Device Applications", *Proc. IEEE Ultrasonic Symp.*, 249–252 (1992).

K. Kaya et al, "Synthesis of AlN Thin Films on Sapphire Substrates by Chemical Vapor Deposition of $AlCl_3$—$NH_3$ Systems and Surface Acoustic Wave Properties", *Jpn. J. Appl. Phys.* vol. 35, 2782–2787, (1997).

G. Carlotti et al., "The Elastic Constants of Sputtered AlN Films", *Proc. IEEE Ultrasonic Symp., 353*, (1992).

R.L. Baer et al., "STW Chemical Sensors", *Proc. IEEE Ultrasonic Symp. 293–298* (1992).

R.M. White, "Surface Elastic Waves" *Proc. IEEE, 58, 1238–1276* (1970).

B.A. Auld et al., "Surface Transverse Wave Propagation Under Metal Strip Gratings", *Proc. IEEE Ultrasonic Symp., 261*, (1986).

C. Campbell, "Surface Acoustic Wave Devices and Their Signal Processisng Applications", *Academic Press Inc.*, (1989) (Chapter 18).

M. Tom–Moy et al., "Atrazine Measurements Using Surface Transverse Wave Devices", *Anal. Chem., 1510–1516*, (1995).

Q. Zhao et al., "Development of Wide Bandgap Semiconductor Photonic Device Structures By Excimer Laser Micromachining", *MRS Internet J. Nitride Semicond. Res. 5S1, W11.69* (2000).

G.W. Auner et al., "Characterization of Aluminum Nitride Thin Films Grown by Plasma Source Molecular Beam Epitaxy", 362, *SPIE V2428*.

R.Y. Krupitskaya, "Optical Characterization of AlN Films Grown by Plasma Source Molecular Beam Epitaxy", *J. Appl. Phys., V84(5), 2861*, (1998).

M.P. Thompson et al., "Epitaxial Growth of Zinc–Blende AlN on Si (001) Substrates by Plasma Source Molecular Beam Epitaxy", *Proceedings of Spring Materials Research Society*, San Francisco, CA (1999).

G.W. Auner et al., "Microstructure of Low temperature grown AlN thin filsm on Si (111)" *J. Appl. Phys. 85, 7879* (1999).

S. Ballandras et al., "New Results on Surface Transverse Wave Resonators Built with Different Combinations of Groove and Strip Gratings", *IEEE Ultrasonics Symp. Proc., 217*, 1998.

L.J. Patgridge, "Production of Catalytic Antibodies Using Combinatorial Libraries", *Biochem Soc Trans 21(4), 1096* (1993).

P.K. Kuo et al., "Generation of a Large Combinatorial Library of the Immunoglobulin Repertoire in Phage Lambda", *Science, 246, 1275* (1989).

International Search Report to International Application PCT/US03/11773.

International Search Report to International Application PCT/US03/11775.

International Search Report to International Application PCT/US03/11863.

* cited by examiner

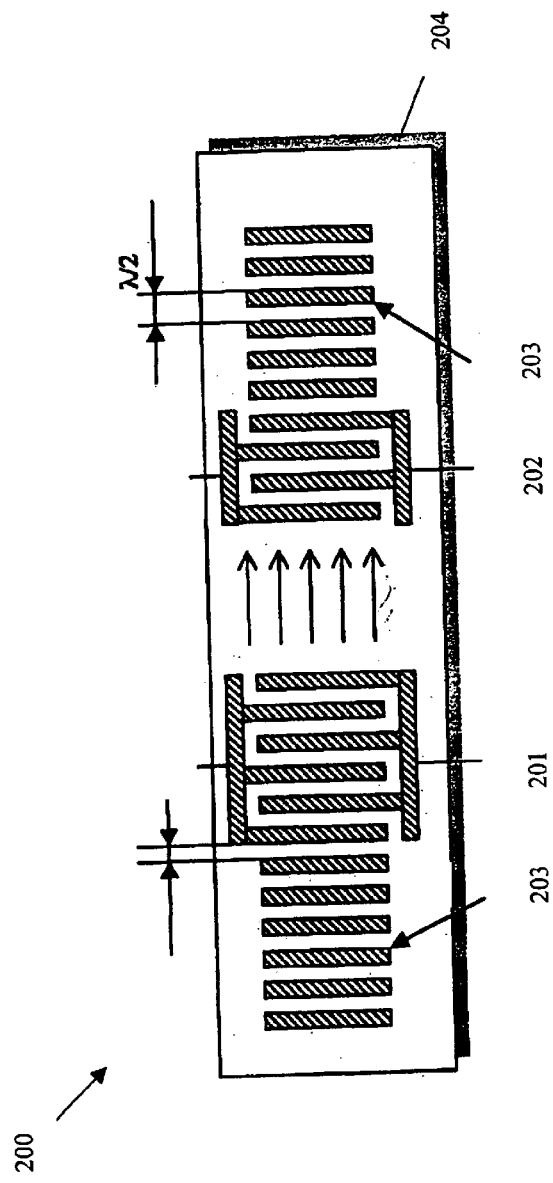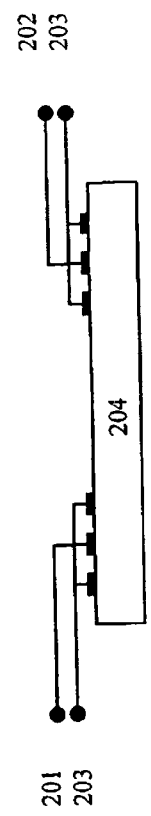
Figure 2a
Figure 2b

| Biosensor Surface Material | Linking Chemistry |
|---|---|
| Gold (Au) | (Dithiobis succinamidyl propionate (DSP) Pierce cat.#22585 |
| Aluminum Nitride (N-succinimidyl 6-[4'- azido-2-nitrophenylamino] hexanoate | (SANPAH) Pierce #22600zz |
| Magnetic Bead mediated linkage | Streptavidin beads linked to MAb via a poly-ethylene oxide maleimide activated biotin linker (PEO) Pierce #21901 |
| Langmuir Blodgett Polymer monolayer With amine functional group | 1 ethyl 3(3-dimethyl aminopropyl) carbo-diamide hydrochloride (EDC) Pierce #22980 |

Figure 15

| Environmental Analyte Structural Classes | Pollutant Source | Monoclonal Antibody Available |
|---|---|---|
| Alkane Hydrocarbons (pentane to hexadecane) | Leaking gasoline storage tanks | No |
| Branched Alkanes (iso-octane To pristane) | Leaking gasoline storage tanks | No |
| Monoaromatics (BTEX) | Industrial waste and failure Of storage/containment systems | Yes (Toluene, Biodesign International, K82313R) |
| Polycyclic Aromatics Phenanthrene, napthalene | Power plant gas effluents, Harbor sediments | No |
| Chlorinated Aliphatics (TCE, PCE, DCE, Methylene Chloride) | Electronic, dry cleaning, Pharmaceutical and chemical industry effluents | No |
| Polychlorinated Biphenyls (eg. CB-138) | Leaking and discarded Capacitors and insulators | No |
| Pesticides and Herbicides | Agricultural contaminated groundwaters | Yes |

Figure 16

ACOUSTIC WAVE SENSOR APPARATUS, METHOD AND SYSTEM USING WIDE BANDGAP MATERIALS

FIELD OF THE INVENTION

The present invention concerns the use of acoustic wave (AW) sensors to detect chemical and biological analytes.

BACKGROUND INFORMATION

Acoustic wave sensors use a detection arrangement that is based on perturbations to mechanical or acoustic waves. As an acoustic wave propagates through or on the surface of the acoustive wave sensor material, any changes to the physical or chemical characteristics of the wave path may affect the velocity and/or amplitude of the acoustic wave. These changes may be correlated to the corresponding physical, chemical, or biological quantities being measured to provide sensing.

Recreational inland lakes, public beaches, and parks, which may be designated for recreational purposes including fishing, swimming, etc., may be closed if there are sufficiently high levels of bacterial contamination, or other sufficiently high levels of chemical, heavy metal, and biological contaminants. At present, continuous monitoring of both bacterial and chemical contaminants may not be available. A source of certain environmental problems, which may lead to restrictions of watersheds for human use, may result from sufficiently high levels of Coliform bacteria, in particular, *Escherichia Coli*. Such levels of this bacteria may be detected by routine sampling or when a public health incident indicates there may be such biological contamination. It may take about 2 days to culture the water samples and determine the basis for any such quality problems. It is believed the detection of chemical and bacteria contamination of drinking and recreation waters would be useful.

There may be various biological and chemical sensors, using fiber optics, chemical interactions, and various fluorescence approaches. Such sensors may, however, have various weaknesses, such as, for example, low sensitivity, selectivity, or an inability to be hybridized or integrated into sensing chip technology. Acoustic wave (AW) sensors, however, may be better suited for use in biological and chemical detection. As discussed in D. S. Ballantine, R. M. White, S. J. Martin, A. J. Ricco, E. T. Zellers, G. C. Frye, H. Wohltjen, "Acoustic Wave Sensor—Theory, Design, and Physico-Chemical Applications", Academic Press, (1997), acoustic wave sensors may use piezoelectric crystals, which may allow transduction between electrical and acoustic energies. The AW sensor may use piezoelectric material to convert a high frequency signal into an acoustic wave, and the higher frequency may enable the sensor to be more sensitive to surface perturbations.

Piezoelectric materials used for acoustic wave sensors may include quartz ($SiO_2$), lithium niobate ($LiNbO_3$), zinc oxide (ZnO), and others. Each of these materials may possess specific advantages and disadvantages, which may relate to, for example, cost, temperature dependence, attenuation, and propagation velocity. Such materials may, however, have limited transverse acoustic wave velocities, low electromechanical coupling coefficients, non-linear temperature coefficients, and may react chemically with the environment. (See the background information in C. Caliendo, G. Saggio, P. Veradi, E. Verona, "Piezoelectric AlN Film for SAW Device Applications", Proc. IEEE Ultrasonic Symp., 249–252, (1992) and K. Kaya, Y. Kanno, I. Takahashi, Y. Shibata, T. Hirai, "Synthesis of AlN Thin Films on Sapphire Substrates by Chemical Vapor Deposition of $AlCl_3$—$NH_3$ Systems and Surface Acoustic Wave Properties", Jpn. J. Appl. Phys. Vol. 35, 2782–2787, (1996) and G. Carlotti et al., "The Elastic Constants of Sputtered AlN Films", Proc. IEEE Ultrasonic Symp., 353, (1992)).

A surface acoustic wave (SAW) sensor may have further disadvantages in liquid if there is sensitivity to viscous damping. In such a case, surface transverse wave (STW) devices may be more suitable in liquid environments. Unlike SAW devices, STW devices use a "shear-horizontal" or "lamb" wave that is horizontally polarized as it propagates across a surface. Accordingly, STW sensors may operate in liquid while maintaining a high mass sensitivity without severe attenuation. (See R. L. Baer, C. A. Flory, M. Tom-Moy, D. S. Solomon, "STW Chemical Sensors", Proc. IEEE Ultrasonic Symp. 293–298 (1992)). There may be other acoustic mode devices that may be suitable for liquid environments, including Shear Horizontal Acoustic Plate Mode (SO-APM) arrangements and Flexural Plate Wave arrangements. Such arrangements may, however, suffer from low mass sensitivity or structure fragility. It is therefore believed that STW arrangements may be better adapted for use in biological and chemical detection.

SUMMARY OF THE INVENTION

The exemplary embodiments and/or exemplary methods of the present invention involve the use of wide BANDGAP aluminum nitride (AlN) semiconductor materials in acoustic wave (AW) devices for use as chemical and biological sensors. Compared to other piezoelectric materials that may be used for AW devices, it is believed that aluminum nitride (AlN) may provide advantages because of its relatively fast acoustic velocity, high electromechanical coupling coefficient, near linear temperature coefficient, and/or high stability in relatively harsh environments. Furthermore, it is believed that AlN may permit hybrid integration of the AW sensors with other VLSI electronics because of the compatibility of AlN with Si. As such, AlN may provide an appropriate platform for providing ultra-sensitive AW sensors integrated with a microchip.

The exemplary AlN-based AW sensor or biosensor may provide further benefits. A biosensor may include receptor molecules integrated with a transducer for use in detection. Any intrinsic selectivity may arise from the specific nature of bio-recognition reactions (such as, for example, antibody-antigen, enzyme-substrate, complementary DNA strands, etc.), and may depend on the coupling between the recognition reaction and the transducer, as well as the inherent sensitivity of the transducer. Using an AlN-based acoustic wave arrangement as a common sensor platform for integration with the sensing medium, immobilization layer polymer viscoelectric properties or metal mechanical properties of the wave arrangement may result in significant changes in such acoustic wave characteristics when the arrangement contacts liquid. Moreover, the motion at the surface of the arrangement may entrain a liquid layer at the surface and propagate a damped shear wave into the liquid. Thus, an AlN-based AW biosensor may operate not only as a SAW-based arrangement (SAW mode), but also as a STW-based arrangement (STW mode), so as to be operable in an air or liquid environment. In particular, the AlN-based biosensor may operate most, or at least more, sensitively in air via the SAW mode and, additionally, the AlN-based biosensor may operate most, or at least more, sensitively in water via the STW mode. Therefore, different devices may not be required to operate in air and water. Furthermore, such a dual mode operation may be useful in applications such as robotic sensing, in which the biosensor device may provide an ability to discriminate between liquids and solids.

It is believed that advantages of the exemplary embodiments and/or exemplary methods of the present invention may include optimized biosensor devices, improved biosensor arrangement performance, determination of effective sensing media immobilization approaches, and AlN-based biosensors that may be used to provide continuous, in-situ, and rapid detection and quantification of analytes in samples.

In this regard, the exemplary embodiments and/or exemplary methods of the present invention are directed to providing (i) wide bandgap semiconductors; (ii) new processing approaches for forming biosensor structures; (iii) integrating new organic and inorganic immobilization structures and embedding them in chemical and/or biological binding sites; (iv) developing wide bandgap semiconductor wave guide arrangements; and (v) integrating the biosensor arrangement as an array in a sensing architecture and other associated integrated electronics on a chip. Furthermore, integrating such an arrangement on a chip and providing new fabrication technologies may provide an array of other potential chip devices. The present subject matter may also be used in developing other wide bandgap semiconductor and semiconductor-organic arrangements in non-electronic devices on a chip. Rapid detection, remote sensing, and relatively low cost may also be provided. It is believed that AlN-based acoustic wave biosensors may provide reliable and faster detection of specific analytes at a lower cost. Thus, it is believed that the AlN-based sensors may provide a new class of economical and portable biosensor arrangements that may detect desired analytes more sensitively and more rapidly, including their use in continuously monitoring contaminated areas.

An exemplary embodiment of the present invention is directed to providing an acoustic wave sensor to detect an analyte, the sensor including a piezoelectric material including a semiconductor material having a wide bandgap.

An exemplary method of the present invention is directed to operating an acoustic wave sensor, in which an acoustic wave is generated, the acoustic wave is directed to transverse a micro-machined arrangement, a resonating frequency of the micro-machined arrangement is detected, and a presence of an analyte is determined based on the detected resonating frequency, in which the analyte contains a target structure that binds to the micro-machined arrangement.

An exemplary method of the present invention is directed to making an acoustic wave sensor, in which a substrate is ultrasonically cleaned, the substrate is etched in a heated acid mixture to remove damage caused by a mechanical polishing, the substrate is rinsed in de-ionized water and methanol, the substrate is loaded into a plasma source molecular epitaxy growth chamber, the substrate is preheated, and the temperature is raised to grow a layer on the substrate.

An exemplary embodiment and/or exemplary method of the present invention is directed to fabricating acoustic wave sensors employing a photolithography process, in which a bottom layer is coated with a photo-resistant coating, a mask is placed before the photo-resistant coating, the coated bottom layer is exposed to UV, the photo-resistant layer is allowed to polymerize, a metal is applied on the polymerized photo-resistant layer, and the polymerized photo-resistant layer is removed.

An exemplary embodiment of the present invention is directed to an acoustic wave sensor including an arrangement having a resonating frequency, the arrangement including a wide bandgap semiconductor material grown using plasma source molecular beam epitaxy, and an immobilization layer traversing the arrangement, the layer containing a binding site to allow a target structure of the analyte to bind to the arrangement so as to change the resonating frequency.

An exemplary method of the present invention is directed to operating an acoustic wave sensor, in which an acoustic wave is generated, the acoustic wave is directed to transverse an arrangement including a wide bandgap material grown using plasma source molecular beam epitaxy, a resonating frequency of the arrangement is detected; and a presence of an analyte is determined based on the detected resonating frequency, wherein the analyte contains a target structure that binds to an immobilization layer of the arrangement.

BRIEF DESCRIPTION OF THE DRAWINGS

FIG. 2a shows a top view of a surface acoustic wave (SAW) resonator arrangement on a piezoelectric substrate.

FIG. 2b shows a side view of the surface acoustic wave (SAW) resonator arrangement of FIG. 2a.

FIG. 8b shows a spectrum of X-ray diffraction of the AlN/Sapphire C plane of FIG. 8a.

FIG. 15 shows various coupling chemistries that may be used for binding a monoclonal antibody to the sensor chip surface.

FIG. 16 shows pollutant sources and monoclonal antibodies that may be available for structural classes of environmental analytes.

DETAILED DESCRIPTION

Figure 1A:
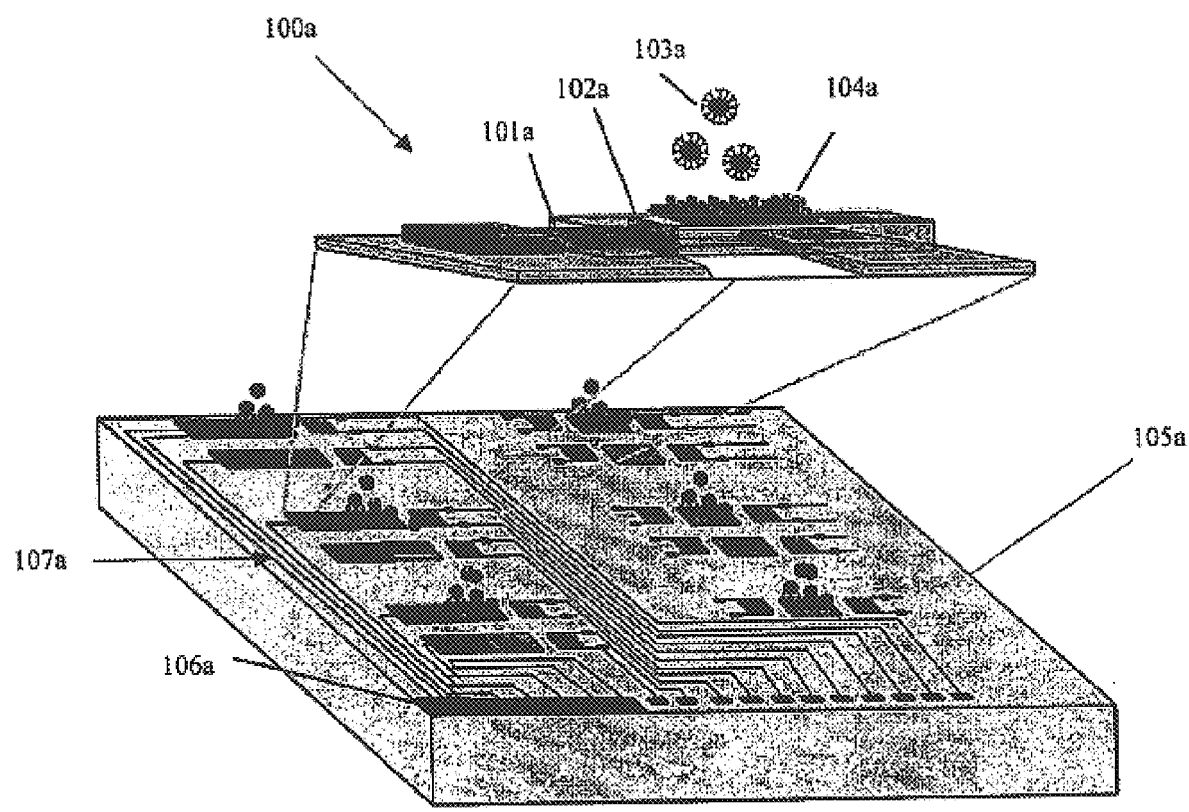
FIG. 1a shows an array arrangement of aluminum nitride-based (AlN) photo-acoustic biosensor devices integrated on a VLSI chip.

FIG. 1a shows an array arrangement of aluminum nitride-based (AlN) photo-acoustic biosensor devices integrated on a VLSI chip 105a. The array arrangement includes an integrated laser diode arrangement 106a capable of high frequency modulation, a waveguide arrangement 107a, an array of acoustic wave arrangements 100a (one is shown in expanded detail arrangement), a carbon-implanted region 102a, and a micro-machined resonating bridge 104a. An immobilization layer containing chemical and/or biological binding sites transverses the resonating bridge 104a. Interaction by an analyte 103a containing target molecules or structures binds to the resonating bridge 104a of the acoustic arrangement 100a, so as to change the resonate frequency. The change in the resonant frequency is detected by reflection using a second laser diode and a return path (such as, for example, using a waveguide) or by electronic interdigital electrodes.

During operation, the laser diode 106a pulses light in the AlN-based waveguide arrangement 107a to the array of acoustic wave devices 100a. Laser light 101a is absorbed at the carbon-implanted region 102a, so as to generate an acoustic shear wave that transverses the resonating bridge 104a. The resonating bridge 104a vibrates or resonates at a frequency of f. The binding of the analyte 103a to the surface causes a frequency change $\Delta f$ equal to $-2.3 \times 10^6 \, f^2 \, \Delta M/A$ where f is the driving frequency in MHz, M is the mass in gms deposited on the surface, and A is the area in cm$^2$. With a driving frequency in the GHz range (which may be about 1 to 6 GHz), changes of less than 0.1 GHz may be detected, which indicates that the binding of five molecules of 100,000 daltons may be detected. Such sensitivity may be provided, for example, for oxide absorption on a metal. In particular, the acoustic wave arrangement 100a may detect a binding of a monolayer of oxygen to less than 1% of the surface of a 100 $\mu$m×100 $\mu$m detector. Thus, the AlN-based photo-acoustic shear wave arrangement 100a may provide a platform for various chemical and biosensor systems, including for example, those used in environmental monitoring of waterways. Furthermore, the use of photonic waveguide coupling may eliminate or at least reduce noise and cross talk at relatively high frequencies, and may also provide for easier integration with the driver electronics. Thus, an exemplary embodiment may include single micro detectors with integrated selective binding media (antibodies) and integrated electronics and/or communications systems. Another exemplary embodiment may include additional detection media and detection array with multiple detection capabilities on the chip 105a.

Figure 1B:
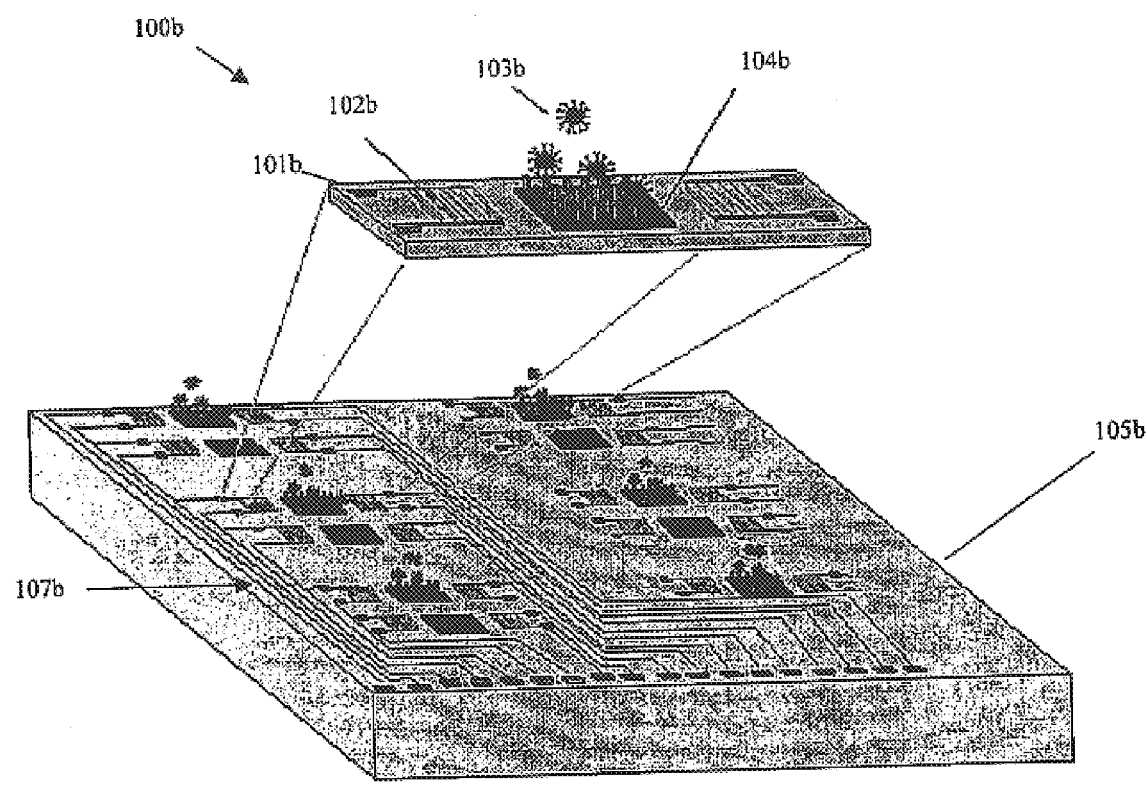
FIG. 1b shows an array arrangement of aluminum nitride-based (AlN) dual mode biosensor devices integrated on a VLSI chip 105b. The array arrangement includes a waveguide arrangement 107b, an array of acoustic wave arrangements 100b (one is shown in expanded detail arrangement), an acoustic wave resonator arrangement 101b, micro-machined energy trapping gratings 102b, and an immobilization layer 104b containing chemical and/or biological binding sites. The acoustic wave resonator arrangement 101b may be arranged to operate in a dual mode (that is, a SAW mode and a STW mode) either by switching from one mode to another or by scanning between modes. Such dual mode operation permits the collection of SAW readings and STW readings either separately or simultaneously.

FIG. 1b shows an array arrangement of aluminum nitride-based (AlN) dual mode biosensor devices integrated on a VLSI chip 105b. The array arrangement includes an array of acoustic wave arrangements 100b (one is shown in expanded detail arrangement), an acoustic wave resonator arrangement 101b, micro-machined energy trapping gratings 102b, and an immobilization layer 104b containing chemical and/or biological binding sites. The acoustic wave resonator arrangement 101b may be arranged to operate in a dual mode (that is, a SAW mode and a STW mode) either by switching from one mode to another or by scanning between modes. Such dual mode operation permits the collection of SAW readings and STW readings either separately or simultaneously.

During operation, interaction by an analyte 103b containing target molecules or structures binds to the immobilization layer 104b so as to change a resonant frequency of the acoustic wave resonator arrangement 101b. The change in resonant frequency may be detected remotely or by an on-board oscillator circuit. An exemplary embodiment of the AlN-based dual mode biosensor device may include a single micro detector with integrated selective binding media (such as, for example, binding media specific to particular antibodies) and integrated electronics and/or communications systems. Another exemplary embodiment may include additional detection media and/or a detection array with multiple capabilities on the chip 105b.

It is believed that aluminum nitride (AlN) is a suitable piezoelectric material for acoustic sensor arrangement because of its relatively high acoustic velocity and electromechanical coupling coefficient, near linear temperature coefficient, resistance to most acids, compatibility with silicon-based technologies, and wide bandgap optical properties that transmit deep UV. The AlN semiconductor material may have a bangap of 6.2 eV, and AlN may be used as a highly sensitive detector for gases or organic components, and may also be used as the frequency-determining element of an oscillator circuit arrangement. A mass change of the coating arising from the analyte absorption results in a proportional shift of the oscillation frequency. Also, it is believed that AlN is highly stable in humid and high temperature environments, which is believed to be useful in biochemical sensing. In contrast, surface acoustic wave (SAW) sensors, may suffer excess attenuation when exposed to a liquid sensing environment. The present system provides a biochemical dual mode sensor using AlN on a C-plane Sapphire that may be switched from a SAW to a Surface Transverse Wave (STW) mode of operation.

FIGS. 2a and 2b show a surface acoustic wave (SAW) resonator arrangement 200 on a piezoelectric substrate 204. FIG. 2a shows a top view, and FIG. 2b shows a side view. The SAW resonator arrangement 200 includes input and output interdigital transducers (IDTs) 201, 202 and reflection gratings 203.

Figure 3A:
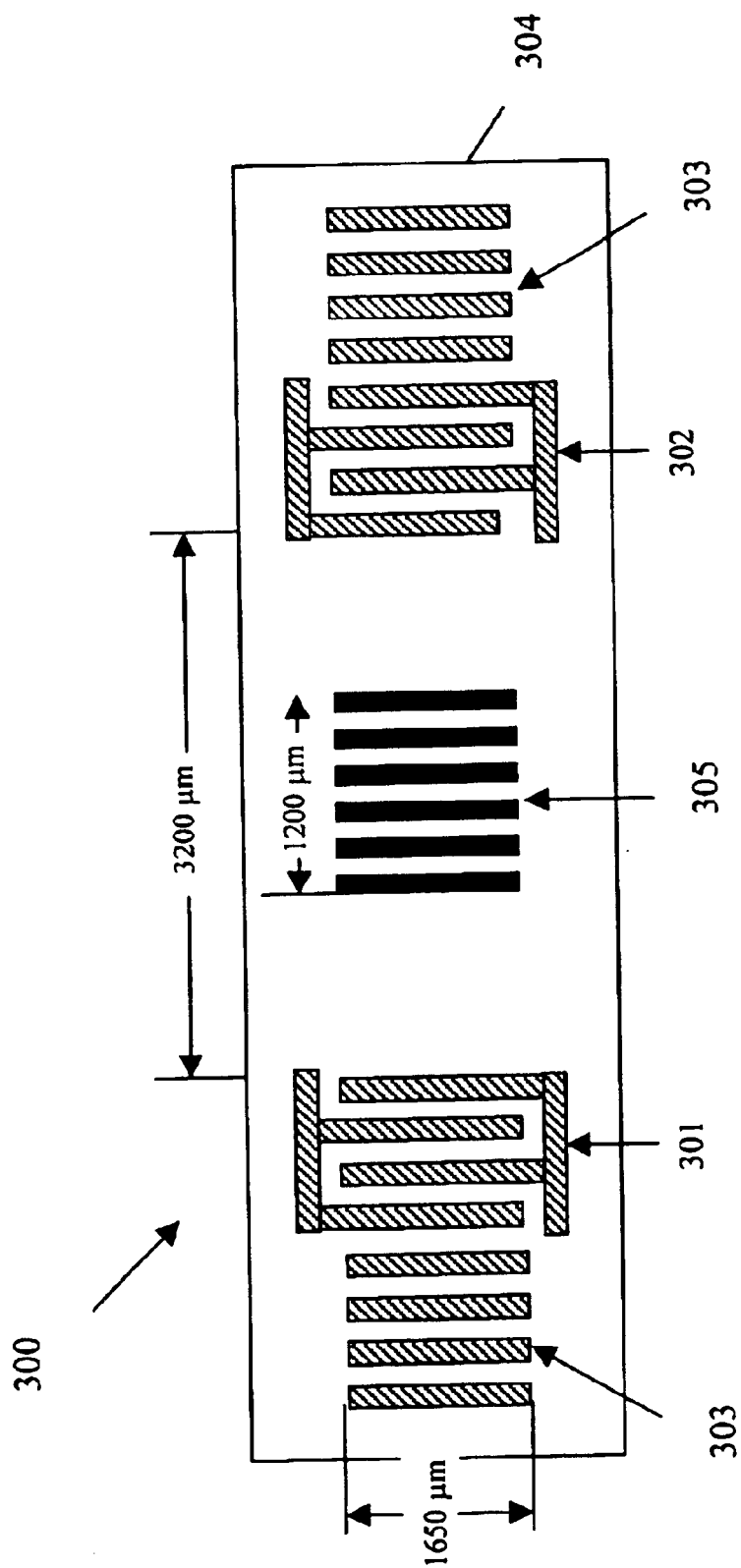
FIG. 3a shows a top view of a surface transverse wave (STW) resonator arrangement on a piezoelectric substrate.

FIG. 3a shows a STW resonator arrangement 300 on a piezoelectric substrate 304. As discussed in R. M. White, Proc. IEEE, 58, 1238–1276 (1970), STW resonators may differ from SAW resonators since there are central energy-trapping gratings 305 formed in between the input and output interdigital transducers (IDTs) 301 and 302. The central energy-trapping gratings 305 may be lithographically patterned metal strips or laser micro-machined grooves, and may be used to constrain a bulk wave to propagate in a STW mode with shear horizontal (SO) polarization (see the background information in B. A. Auld, D. F. Thompson, "Surface Transverse Wave Propagation Under Metal Strip Gratings", Proc. IEEE Ultrasonic Symp., 261, (1986)). The acoustic wavelength I of the STW resonator 300 may be, for example, 32 μm.

In an exemplary embodiment, the STW resonator device 300 includes 20 pairs of IDTs 301 with 40 reflector gratings 303 on each side and 120 central gratings 305 in between. The width of each IDT electrode and the spacing between adjacent electrodes may be, for example, 8 μm. The periodicity of the reflection gratings 303 may correspond to the same geometry parameters as that of the IDTs 301. The periodicity of the central gratings 305 may be 10 μm, which corresponds to 5 μm in grating width and spacing respectively. This arrangement of the central gratings 305 may facilitate the transmission of STW rather than reflection (see the background information in C. Campbell, "Surface Acoustic Wave Devices and Their Signal Processing Applications", Academic Press Inc., (1989)). The grating may also be matched to IDTs 301 to prevent reflection (see R. L. Baer, C. A. Flory, M. Tom-Moy, D. S. Solomon, "STW Chemical Sensors", Proc. IEEE Ultrasonic Symp, 293–298 and M. Tom-Moy, R. L. Baer, D. S. Solomon, T. P. Diehard, "Atrazine Measurements Using Surface Transverse Wave Devices", Anal. Chem., 1510–1516, (1995)), or the periodicity of the grating may not be an important design consideration (see Q. Zhao, M. Lukitsch, J. Xu, G. W. Auner, R. Naik, P-K. Kuo, "Development of Wide Bandgap Semiconductor Photonic Device Structures By Excimer Laser Micromachining", MRS Internet J. Nitride Semicond. Res. 5S1, W11.69 (2000)).

Figure 3B:
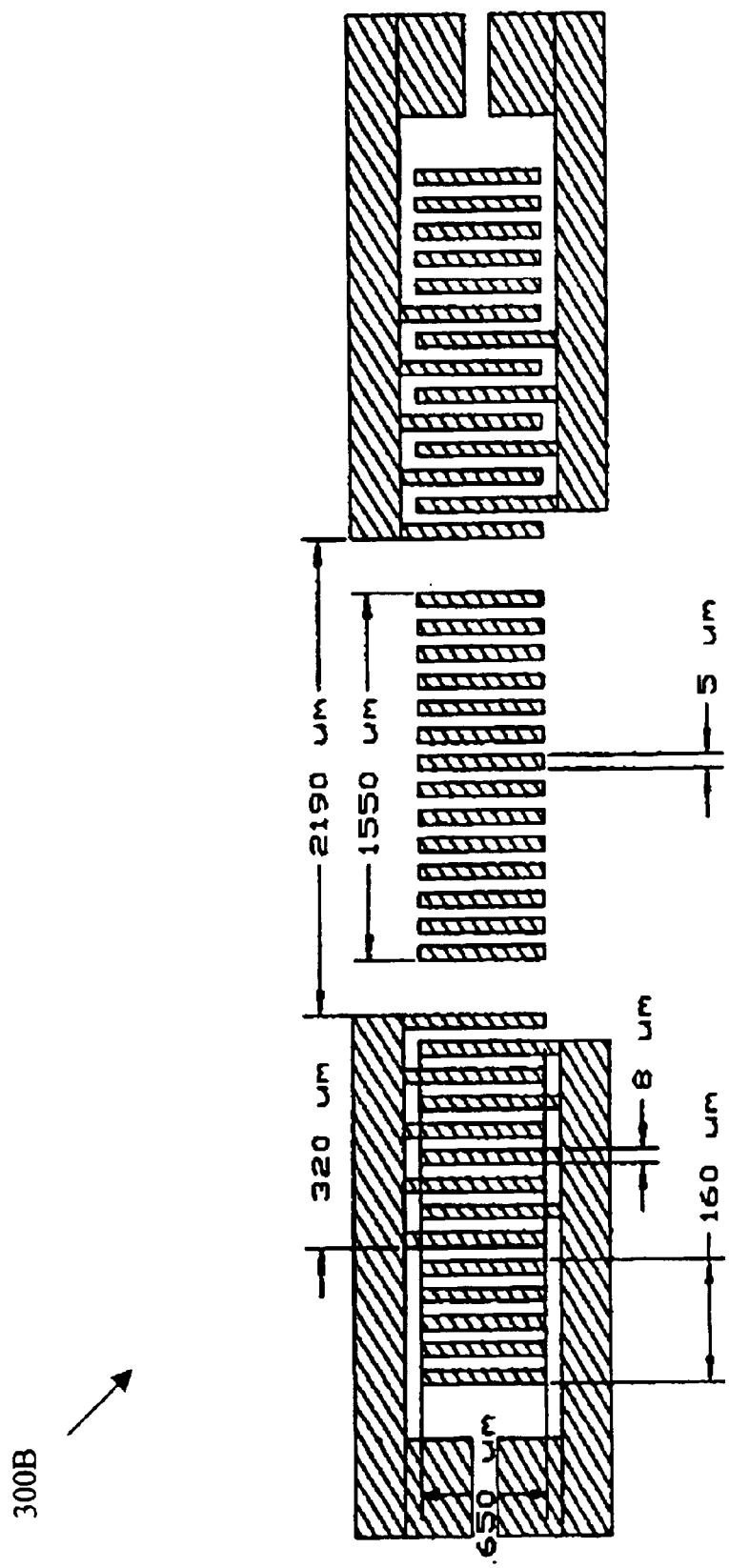
FIG. 3b shows a top view of an AlN/Sapphire acoustic wave resonator arrangement on a piezoelectric substrate.

FIG. 3b shows another exemplary embodiment of an AlN/Sapphire acoustic wave biosensor resonator device 300b. The wavelength (λ) of the resonator is 32 μm. There are 20 pairs of interdigit electrodes (IDTs) with 40 reflectors on each side. The periodicity of the central gratings is 10 μm, the acoustic aperture is 50 λ, and the space between two IDTs is 70 λ. The thickness of Al is about 500 Å. Laser micro-machining may be provided by a KrF Excimer laser (LPX2051) with a 248 nm wavelength. The Excimer laser may provide a precise and flexible micro-machining process for wide band gap semiconductor materials like AlN (see Q. Zhao, M. Lukitsch, J. Xu, G. W. Auner, R. Naik, P-K. Kuo, "Development of Wide Bandgap Semiconductor Photonic Device Structures By Excimer Laser Micromachining", MRS Internet J. Nitride Semicond. Res. 5S1, W11.69 (2000)).

Figure 3C:
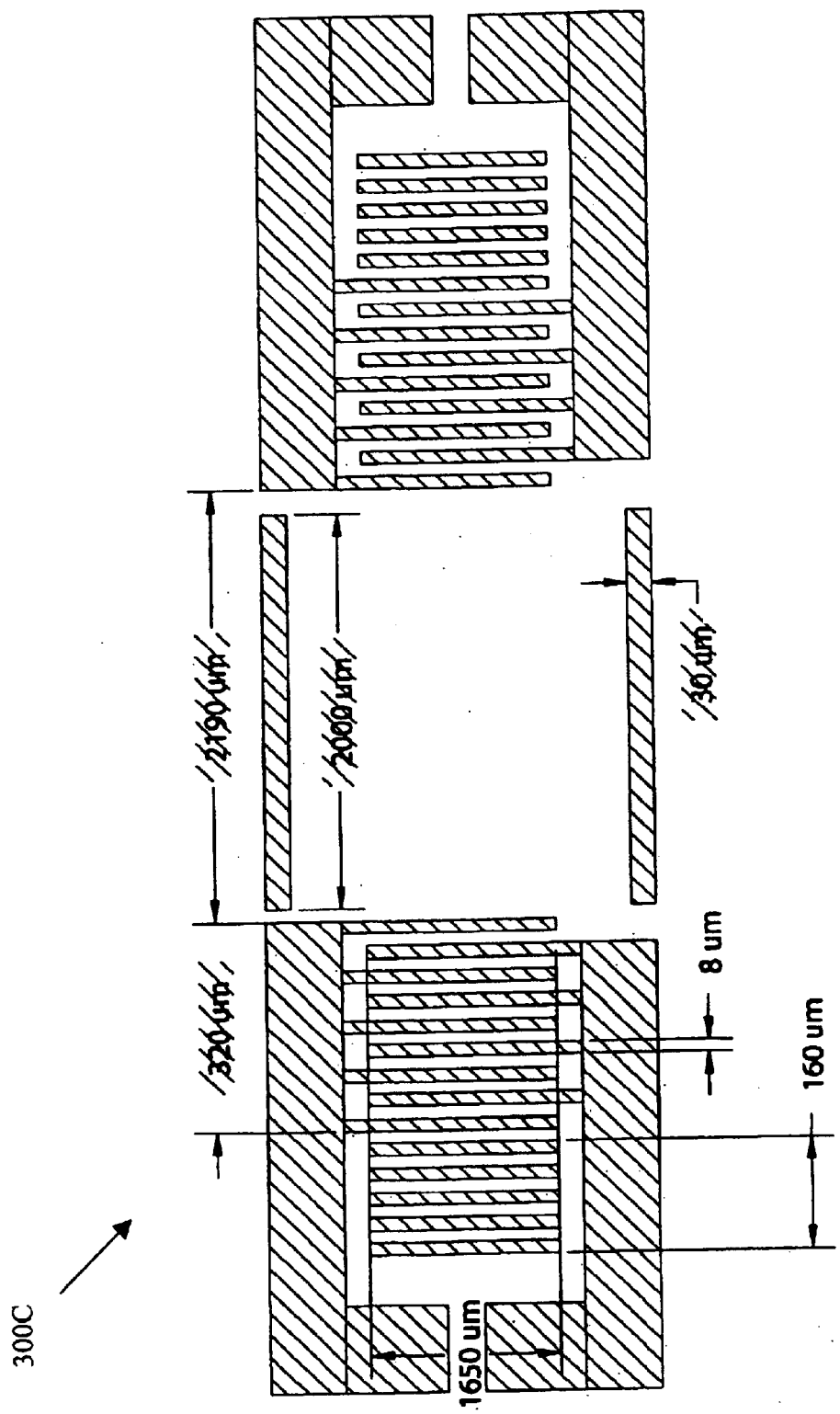
FIG. 3c shows a top view of an AlN/Sapphire acoustic wave resonator arrangement with laser micro-machined sidebars.

FIG. 3c shows another exemplary embodiment of an AlN/Sapphire acoustic wave biosensor resonator arrangement 300C with laser micro-machined sidebars.

The aluminum nitride (AlN) layers or thin films for acoustic wave biosensor arrangements may be grown on sapphire using Plasma Source Molecular Beam Epitaxy (PSMBE). This deposition method may use a magnetically enhanced hollow cathode lined with the target material, which may be an MBE grade aluminum. High quality AlN epitaxial layers may be grown using this system. (see the background information in G. W. Auner, P. K. Kuo, Y. S. Lu and Z. L. Wu, "Characterization of Aluminum Nitride Thin Films Grown by Plasma Source Molecular Beam Epitaxy", 362, *SPIE* V2428 and R. Y. Krupitskaya and G. W. Auner, "Optical Characterization of AlN Films Grown by Plasma Source Molecular Beam Epitaxy", *J. Appl. Phys.*, V84(5), 2861, 1998). The base pressure of the system is maintained in the range of $10^{-9}$ to $10^{-10}$ Torr, and radio frequency (RF) power is supplied to generate plasma inside the hollow cathode. The dynamic pressure during deposition is maintained at $1 \times 10^{-3}$ Torr, and negative acceleration bias is applied to the substrate. The growth temperature, acceleration bias, $N_2$, flow and RF power level may be adjusted to provide optimum thin films.

Figure 4:
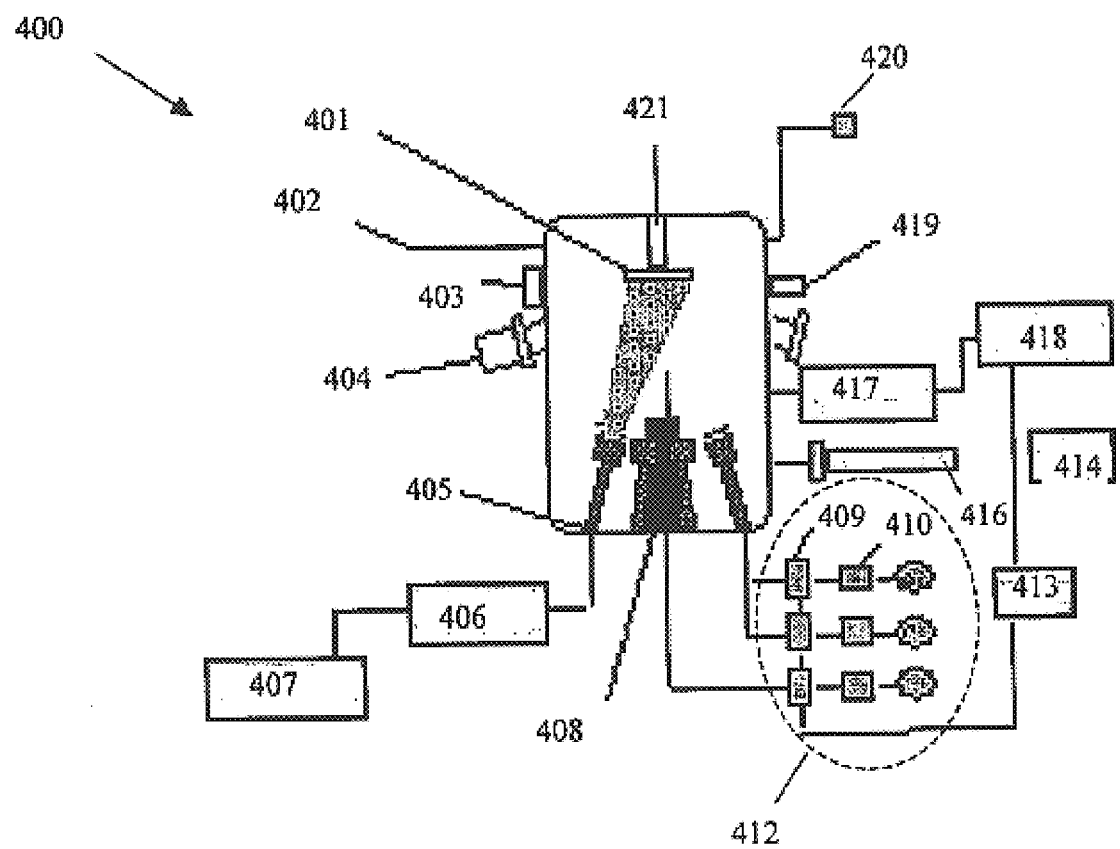
FIG. 4 shows an exemplary embodiment of a Plasma Source Molecular Beam Epitaxy (PSMBE) system.

FIG. 4 shows an exemplary embodiment of a Plasma Source Molecular Beam Epitaxy (PSMBE) system 400. The PSMBE system 400 is a UHV system with a base pressure, for example, in the upper $10^{-11}$ Torr region or lower. The PSMBE system 400 includes a heated rotating substrate holder 401 to hold up to three-inch wafers, a sample transfer to clean room 402, a RHEED screen 403 with CCD camera and computer analysis system, an ellipsometry system 404, a PSMBE source 405, an auto-matching network 406, an R.F. sputtering power supply 407, an IR pyrometer 408 for substrate temperature measurement, a mass flow control system 412 including mass flows 409 and gas purifiers 410, a controller 413, an ion pump 414, a cyropump 416, a differential pump 417, a residual gas analyzer 418, a 35 KeV reflective high-energy electron diffraction system 419 for film analysis, a capacitance manometer 420, and a substrate bias power supply 421.

Figure 5:
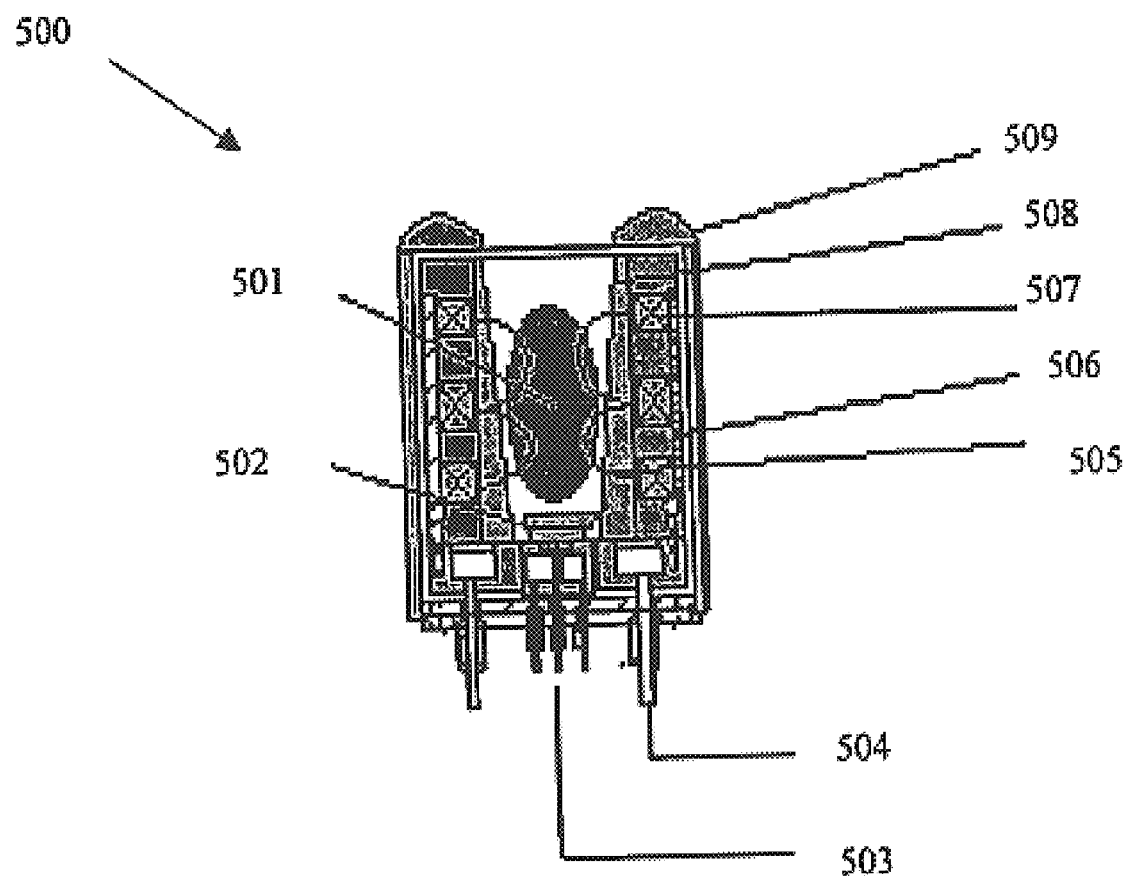
FIG. 5 shows an exemplary embodiment of a hollow cathode deposition system for growth of AlN thin films.

FIG. 5 shows an exemplary embodiment of a hollow cathode deposition system 500 for growing AlN layers or thin films. The deposition system 500 includes an impeller 502, a gas inlet 503, a pulsed dc or rf power 504 that may be integrated with water cooling lines, magnets 507 to produce magnet field lines 505, a magnet return 506, and an anode 509. The deposition system 500 may operate as follows. A nitrogen or nitrogen/argon plasma 501 is formed within the hollow cathode. The walls 508 of the hollow cathode are lined with MBE grade Aluminum (or other deposition material). A r.f. or pulsed dc power 504 to the hollow cathode is used to efficiently form a plasma (due to the hollow cathode effect and magnetically induced effective pressure increase). The plasma 501 dissociates the diatomic nitrogen into radicals and radical ions as well as other combinations. The ions sputter atoms from the cathode surface (in a normal direction.) Multiple collisions may occur for an Al atom or ion to escape the source. The nitrogen and Al ions are accelerated to a specified energy of −12 eV for AlN. The condensing adatoms have highly regulated energy, so that crystal growth may occur even at low substrate temperatures. The AlN crystal growth may be tailored depending on the deposition parameters from polycrystalline, to near single crystal both hexagonal and zinc blende structures, (see M. P. Thompson, G. W. Auner, and A. R. Drews, "Epitaxial growth of zinc-blende AlN on Si (001) susbtrates by Plasma Source Molecular Beam Epitaxy", Proceedings of Spring Materials Research Society, San Francisco, Calif. (1999)). Since the substrates used (Si and Sapphire) may have considerable lattice mismatch, even epitaxial growth may be strained. Using a compliant amorphous AlN underlayer may provide nearly strain-free AlN growth (see the background information in G. W. Auner, F. Jin, V. M. Naik, and R. Naik, J. Appl. Phys. 85, 7879 (1999)). The resulting films may be micromachined into free standing bridge structures if needed.

The fabrication of waveguide structures for the biosensor arrangement may require specialized micro-machining technology to produce a high-density array of devices. In particular, AlN may not be etchable by "traditional" chemical methods. It is believed that concentrated KOH should be a reasonably good etchant. Furthermore, the chemical etching process may be highly anisotropic. Even ion beam and other plasma etching techniques may not be viable solutions due to parasitic (with respect to waveguide performance) damage of the structure. This may be true of diamond films as well. Therefore, to extend the capability to develop sensors based on these wide bandgap semiconducting materials, an EXCIMER surface micro-machining is used to fabricate the piezoelectric optical waveguide and acoustic wave sensor arrangement. In particular, it is believed that short wavelength EXCIMER ablation of AlN may be used to provide highly detailed device structures with sufficiently straight high aspect ratio walls. In addition to fabricating waveguide devices, EXCIMER laser micro-machining may be used to form surface features for receiving a selective immobilization layer containing the detecting medium.

Figure 6:
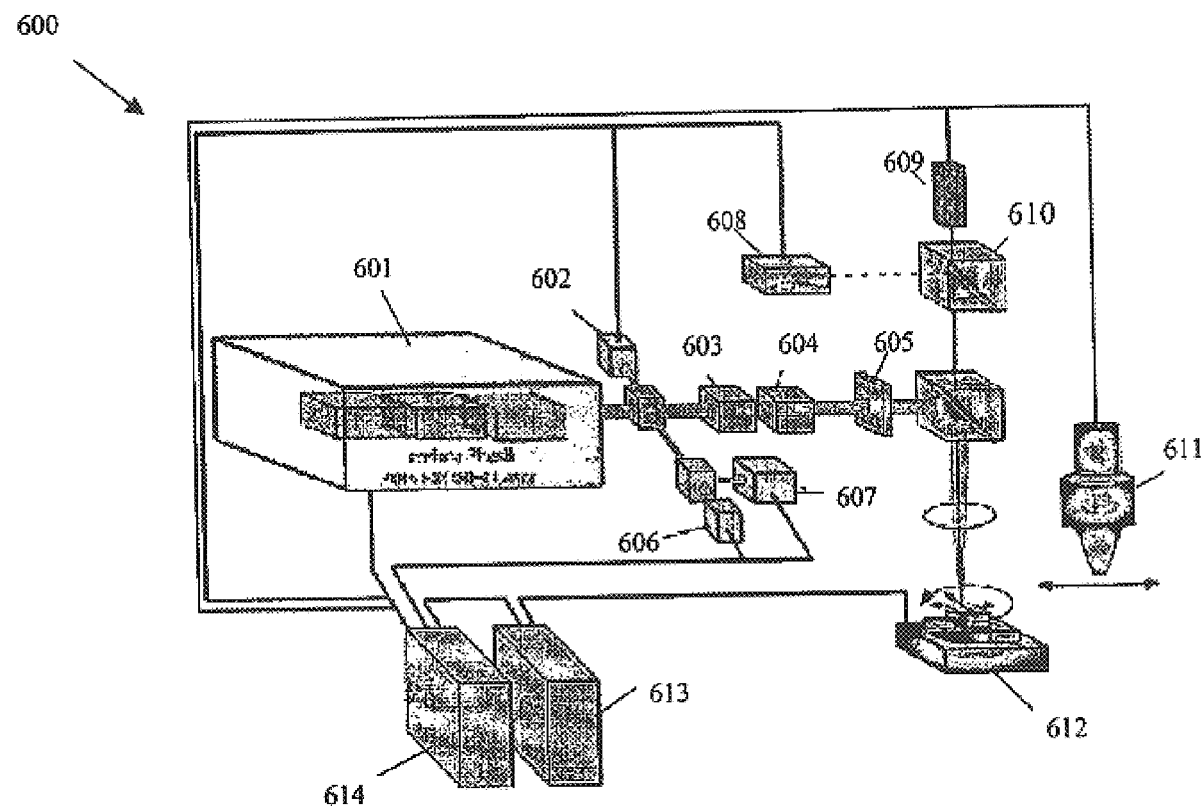
FIG. 6 shows an exemplary embodiment of an EXCIMER laser micro-machining arrangement.

FIG. 6 shows an exemplary embodiment of an EXCIMER laser micro-machining arrangement 600. The system 600 includes an EXCIMER laser 601, a pyroelectric energy sensor 602, an attenuator 603, a homogenizer 604, a mask 605, a beam measuring arrangement 606 to measure the beam intensity and/or time duration, a beam profile measuring arrangement 607 to measure a beam profile, a CCD camera 608, an alignment laser 609, a beam splitter 610, an interferometer 611 for profiling an optical surface, a 25 nm resolution x-y-z-φ motion system 612, a motion control system 613, and a computer (or other processor arrangement) 614. The system 600 is capable of sub-micron steps, repeating ablation features, or a mask 605 may be used for complete device structure machining of the desired features under rapid fabrication conditions.

The waveguide structures produced using EXCIMER laser micro-machining may be of a high quality with clean interfaces. It is believed that using 248 nm wavelength, for example, may provide superior results when compared to lower wavelengths. This may occur even though the bandgap of AlN is 6.2 eV or 196 nm. It is believed that a small amount of energy may be absorbed in the AlN due to defects, which may result in a less destructive machining process.

The use of the EXCIMER laser system 600 to micromachine the acoustic wave biosensor arrangement may be characterized as a function of beam fluence and energy. A surface diffused boron layer may be used in the silicon substrates to act as a chemical etches stop. The EXCIMER laser system 600 may be used to surface micro-machine the waveguide structure down through the boron layer, so as to allow chemical etching to be used to undercut the AlN forming a bridge structure. A Varian Exteron Ion accelerator may be used to implant carbon in a small region at the interface between the waveguide and the acoustic wave bridge. Non-suspended structures on sapphire substrates may be used.

Figure 7A:
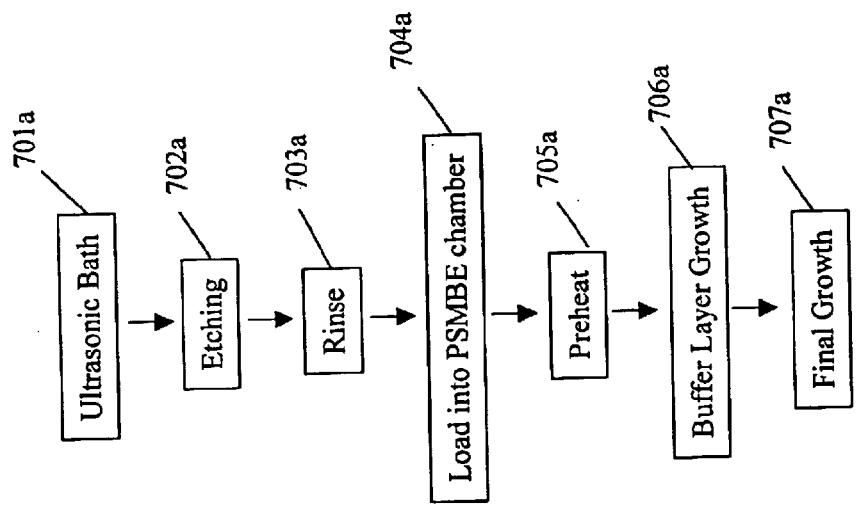
FIG. 7a shows an exemplary method for growing an AlN layer or thin film for use in an acoustic wave biosensor arrangement.

FIG. 7a shows an exemplary method for growing an AlN layer or thin film for use in making the acoustic wave biosensor arrangement. In step 701a, a C-plane Sapphire substrate is ultrasonically cleaned in Trichloroethylene, Acetone and Methanol for 15 minutes sequentially. In step 702a, the sapphire substrate is etched in a heated (80° C.) acid mixture ($H_3PO_4$:$H_2SO_4$:=1:3) for 1 hour to remove the damage caused by mechanical polishing. In step 703a, the substrate is rinsed in de-ionized water and methanol, and may also be blown dry. In step 704a, the sapphire substrate is loaded into a PSMBE growth chamber via a load lock. Before starting the growth, the sapphire substrate is first preheated to 800° C. for an hour in step 705a. In step 706a, the substrate is permitted to cool down to 400° C. to start buffer layer growth for 3 hours. Finally, in step 707a, the temperature is raised to 650° C. to begin normal growth. During step 707a, the R.F. power is set to 200 W and the $N_2$ and Ar flow ration is kept at 10:40 seem. The resulting thickness of AlN film growth may be, for example, 1.4 μm.

Figure 7B:
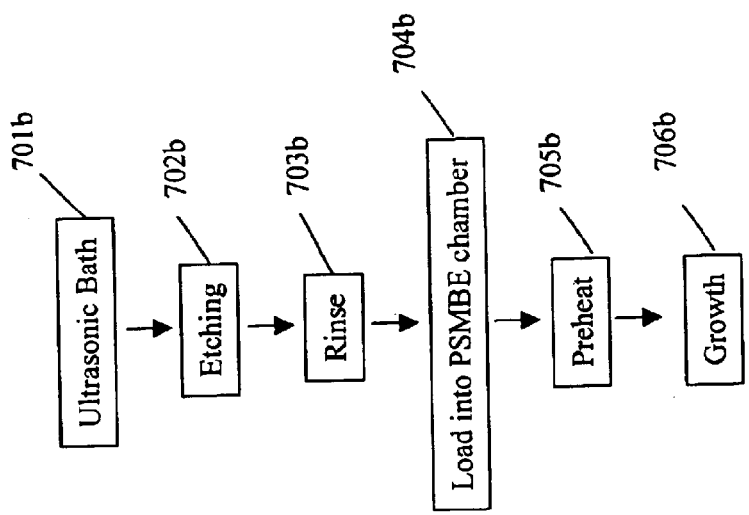
FIG. 7b shows another exemplary method for growing an AlN layer or thin film.

FIG. 7b shows another exemplary method of the present invention for growing an AlN layer or thin film in fewer steps. In particular, steps 706a and 707a have been combined into one step. More specifically, in step 701b, a C-plane sapphire substrate is ultrasonically cleaned followed by the same procedures of step 701a. In step 702b, as in step 702a, acid etching ($H_3PO_4$:$H_2SO_4$=1:3) may then be applied for 1 hour at 80° C. to remove any damage from mechanical polishing. In step 704b, as in step 704a, the sapphire substrate is loaded into a PSMBE growth chamber via the load lock. Before starting the growth, the sapphire substrate is first preheated to 650° C. in step 705b. Finally, in step 706b, growth occurs at 650° C. for 24 hours. The resulting thickness of the AlN layer or film may be, for example, 2.2 μm.

Figure 8A:
FIG. 8a shows an in-situ Reflection High Energy Electron Diffraction (RHEED) image of a AlN/Sapphire C plane.
Figure 8B:
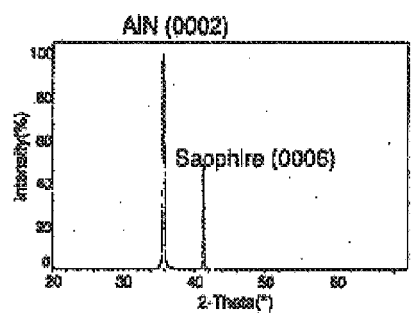

The AlN thin film growth may be characterized in-situ using Reflection High Energy Electron Diffraction (RHEED), and X-ray diffraction spectrometry may be used to determine the structure of thin films. FIG. 8a shows an in-situ RHEED image of a grown AlN/Sapphire C plane. The sharply distinguishing pattern suggests that the film is crystalline and smooth. A spectrum of X-ray diffraction, which is shown on FIG. 8b, also indicates that the AlN layer or film is highly C-axis oriented.

Figure 9:
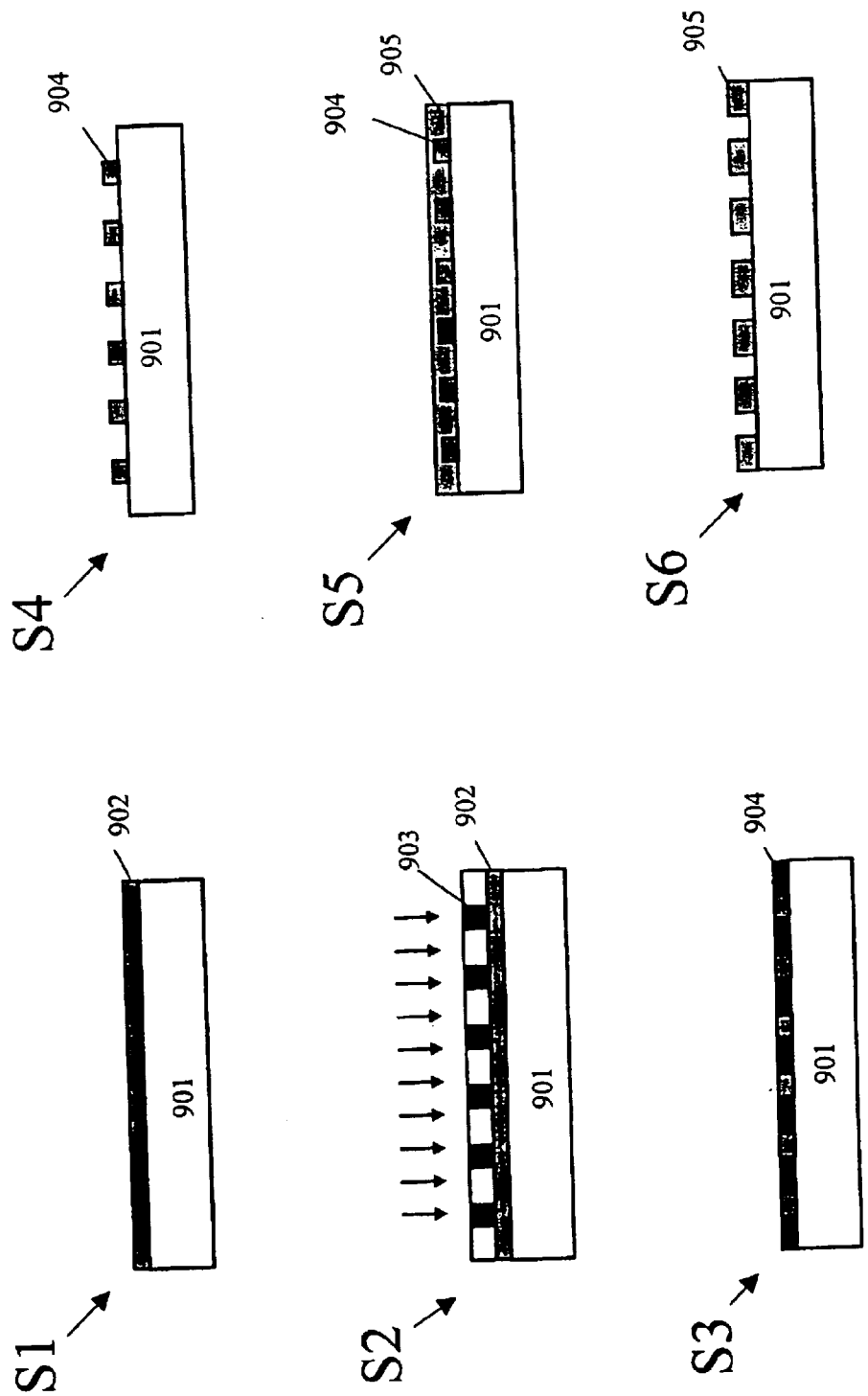
FIG. 9 shows an exemplary photolithography lift-off method to fabricate an acoustic wave biosensor arrangement with a desired pattern.

FIG. 9 shows an exemplary photolithography lift-off method to fabricate an acoustic wave biosensor arrangement with a desired pattern. In step S1, AlN or $Al_2O_3$ bottom layer 901 is coated with a photoresistant coating 902. In step S2, the desired pattern is transferred by placing mask 903 before the photoresistant coating 902. In step S3, the layer(s) are exposed to UV. In step S4, a polymerized photoresistant layer 904 is developed. In step S5, a metal 905 is applied, and in step S6, the polymerized photoresistant layer 904 is removed.

Figure 10A:
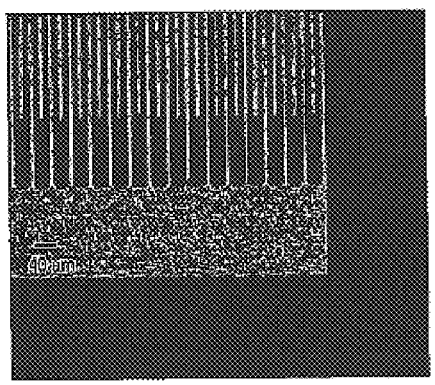
FIG. 10a shows an optical image of an acoustic wave biosensor device after photolithography.
Figure 10B:
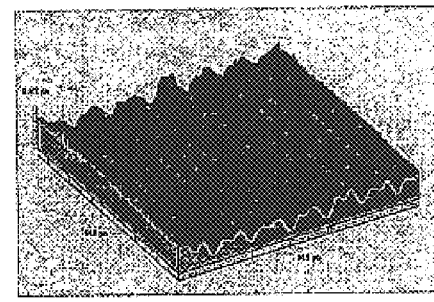
FIG. 10b shows an Atomic Force Microscopy (AFM) image of laser micro-machined groove gratings.
Figure 10C:
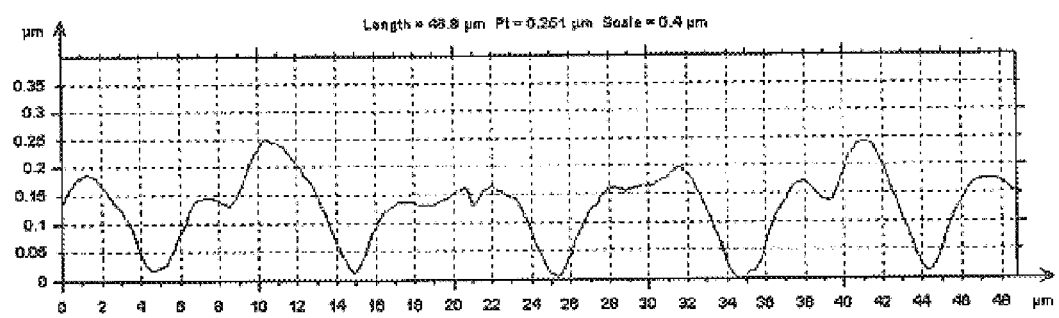
FIG. 10c shows a line profile of laser micro-machined groove gratings.

Also, FIG. 10*a* shows an optical image of an acoustic wave biosensor device after photolithography. The patterns are clean and distinguishable. An optical microscope may be used to examine the quality of devices after photolithography. Atomic Force Microscopy (AFM) may be used to evaluate the laser micro-machined groove gratings. FIGS. 10*b* and 10*c* show an AFM image and a line profile of laser micro-machined groove gratings. The microgrooves are 5 μm wide, 1500 Å in depth and have a periodicity of 10 μm. The grooves are relatively sharp, although there may be some anomalies on the surface that may be caused by laser thermal ablation.

Figure 11:
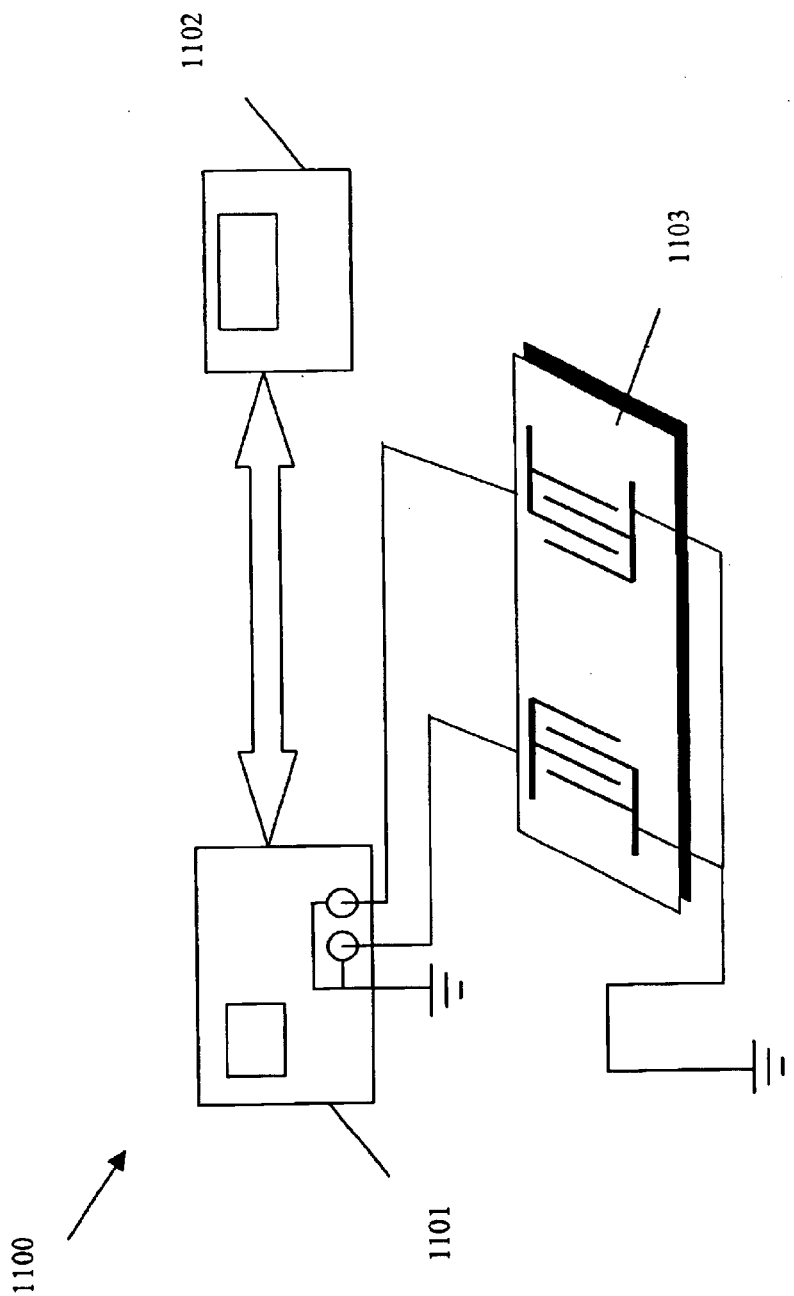
FIG. 11 shows an test station to evaluate the performance of acoustic wave biosensor devices.

FIG. 11 shows a test station 1100 to evaluate the performance of an acoustic wave biosensor device 1103. Test station 1100 may include a computer or other processor arrangement 1102. The test station 1100 may include a Signitone submicron probing station, and it may also include long working distance optical microscope features with integrated high frequency pulsed laser probe and microwave microprobes, as well as an array of other electrical and optical measurement equipment. The test station 1100 may operate in either an optical or an electrical mode. The test station 1100 may be used to assess device performance and to determine device specifications prior to VLSI design and fabrication. The resulting device structures may be developed into biosensor arrangements by adding organic detecting media. For example, the organic detecting media may include a specific phage for plague, cholera, etc.

Figure 23:
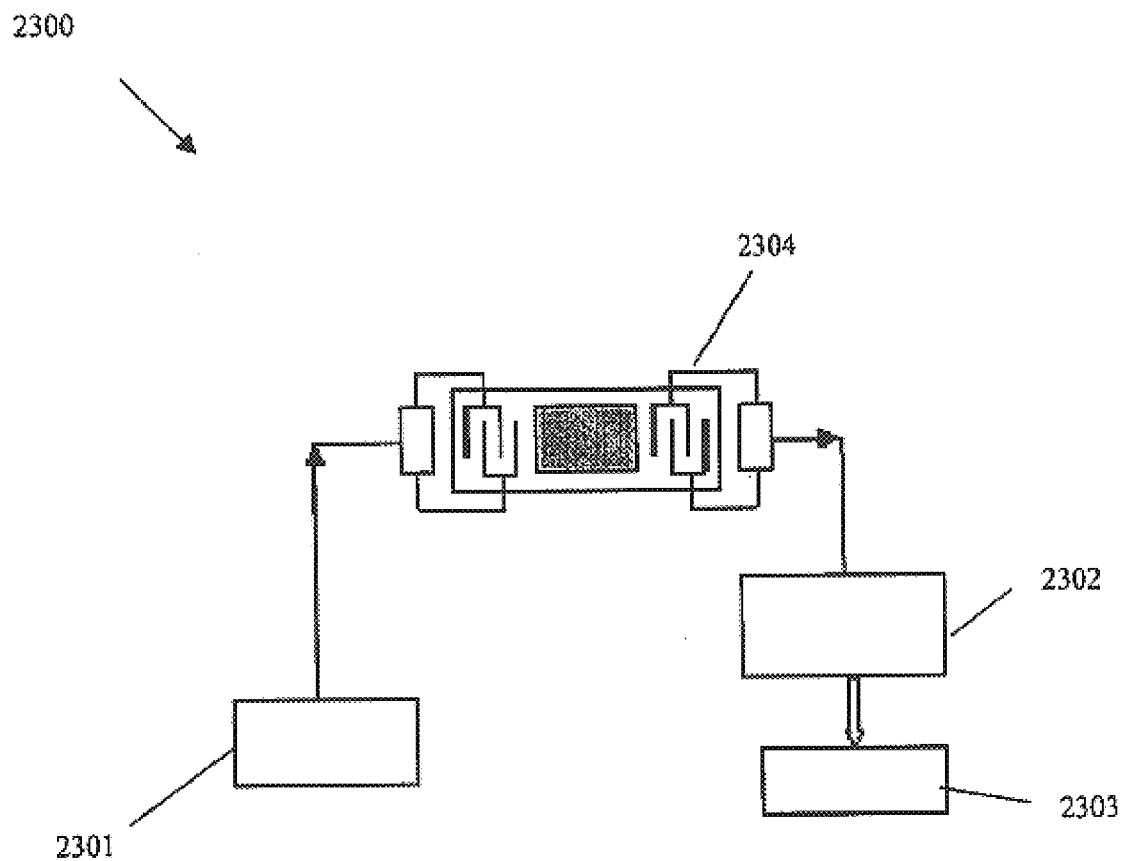
FIG. 23 shows a propagation measurement arrangement.
Figure 24:
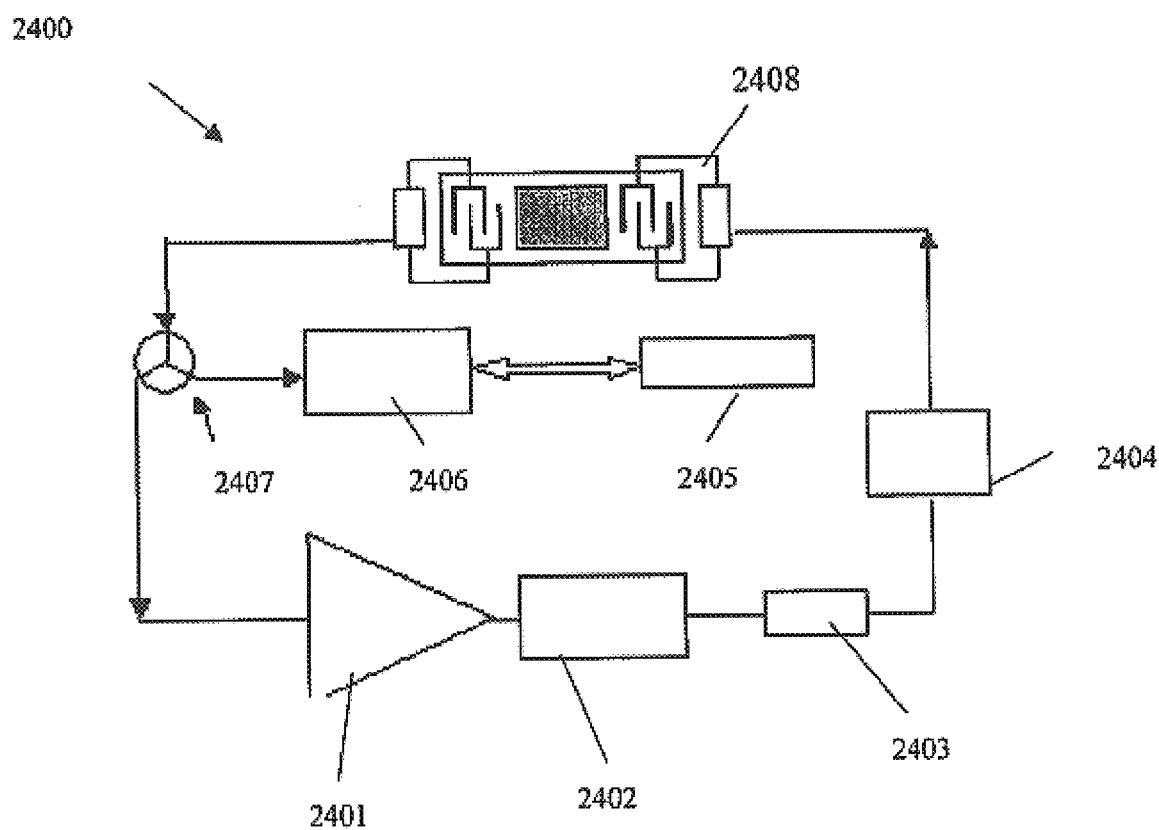
FIG. 24 shows an oscillator loop based measurement arrangement.

Still further, FIG. 24 shows an oscillator loop based measurement arrangement 2400. The frequency counter 2302 of FIG. 23 is replaced by a vector voltmeter across the input and output IDTs 2408 using a power splitter 2407 so that both amplitude changes and phase (frequency) shift between the IDTs 2408 may be obtained. The AW device 2408 may be considered a feedback path for the amplifier (AMP) 2401. To reach stable operation, the round trip phase shift in the closed loop should equal the integer multiple of 2π, and the gain of the chosen AMP 2401 should be greater than or at least equal to the insertion loss of the device 2408 at the operating frequency. An automatic gain control 2403 circuit may be used with the AMP 2401 to maintain the oscillation amplitude and a phase shifter 2404 may be used to better ensure the required phase compensation. A bandpass filter 2402 excludes any harmonics generated by the AMP 2401, so as to avoid false input to frequency counter 2406 and associated computer 2405. In contrast to the oscillator loop based measurement arrangement, propagation measurements may not provide the same sensitivity but may not be subject to mode hopping associated with an oscillator circuit under certain circumstances.

The optical test station 1100 may include a network analyzer 1101, such as, for example, a HP8753D network analyzer, to analyze propagation properties of acoustic wave biosensor devices. The network analyzer 1101 provides a controlled-amplitude signal to the input of a testing device or circuit arrangement over a range of frequencies, and measures the output of the device or circuit arrangement in terms of its magnitude and phase relative to the input as a function of frequency. The HP8753D network analyzer has a frequency range of 30 kHz to 6 GHz, which should be sufficient for characterizating the AW devices.

Figure 12B:
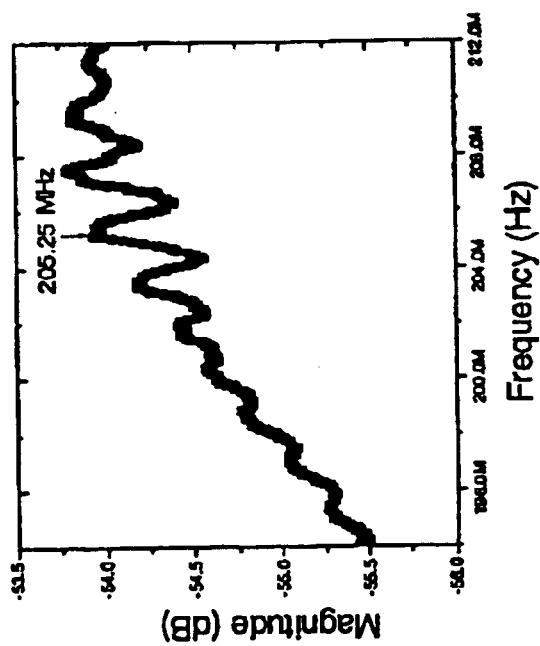
FIG. 12b shows an analysis of the same dual mode AlN/Sapphire acoustic wave biosensor device operating in an Surface Transverse Wave (STW) mode.
Figure 12A:
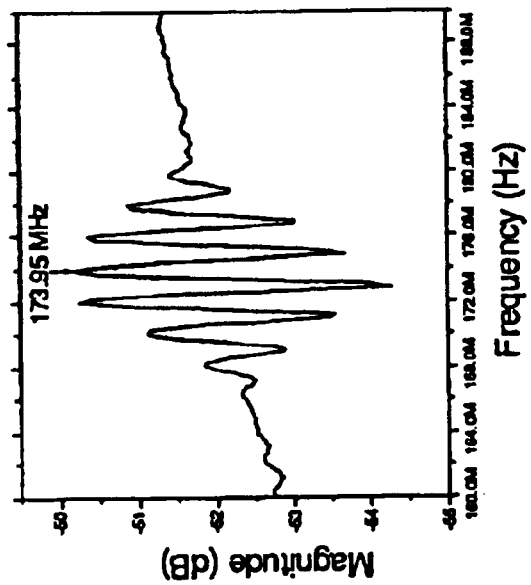
FIG. 12a shows an analysis of a dual mode AlN/Sapphire acoustic wave biosensor device operating in a Surface Acoustic Wave (SAW) mode.

FIG. 12*a* shows an analysis of an AlN/Sapphire acoustic wave biosensor device operating in a Surface Acoustic Wave (SAW) mode. As shown, the resonance frequency for SAW is at 173.95 MHz, which corresponds to a phase velocity of 5566 m/s by using the relation $v = f_{res} \lambda_{res}$. In addition to SAW resonance, STW resonance may be established in the biosensor device due to its Al metal strip and microgroove central gratings structure. A device without such central grating features does not produce STW resonance. As discussed in C. Campbell, *Surface Acoustic Wave Devices and Their Signal Processing Application*, 454, (Academic Press, Inc., 1989) and S. Ballandras, E. Bigler, W. Daniau, J. Py, A. Pakfar, G. Marianneau and G. Martin, "New Results on Surface Transverse Wave Resonators Built with Different Combinations of Groove and Strip Gratings", IEEE Ultrasonics Symp. Proc., 217, 1998, the central grating structure may operate to constrain the bulk wave to propagate as a surface transverse wave (STW) with shear horizontal (SH) polarization. FIG. 12*b* shows an analysis of the same AlN/Sapphire acoustic wave biosensor device operating in an STW mode. As shown, the central frequency of STW is 205.25 MHz, which corresponds to a phase velocity of 6568 m/s.

Figure 13:
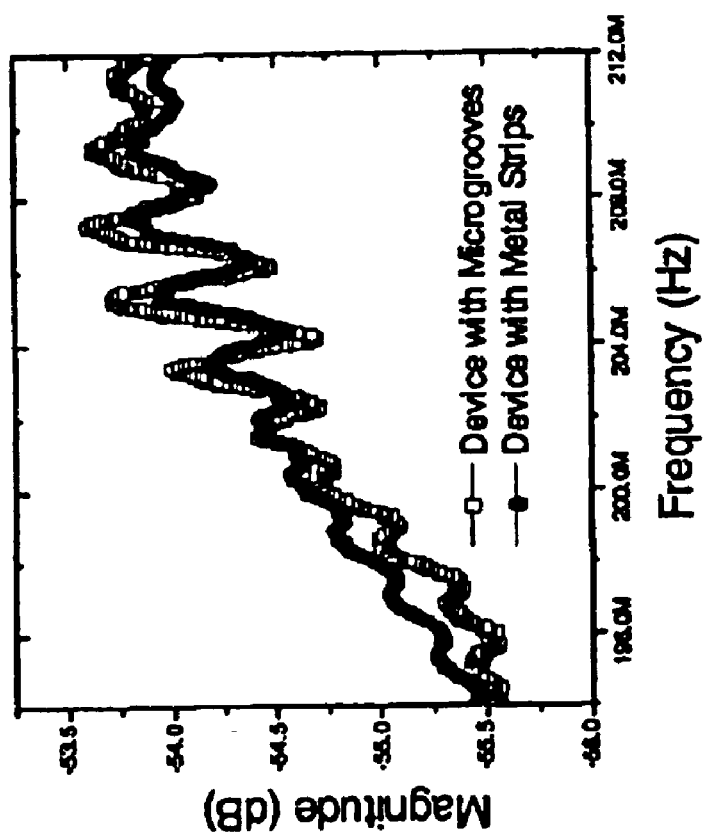
FIG. 13 shows an analysis of a dual mode AlN/Sapphire acoustic wave biosensor device to show the effect of grating structures on STW propagation.

FIG. 13 shows an analysis of AlN/Sapphire acoustic wave biosensor device to show the effect of grating structures on STW propagation. It has been found that laser micromachined grooves may enhance STW resonance as compared to classical metal strips.

Figure 14B:
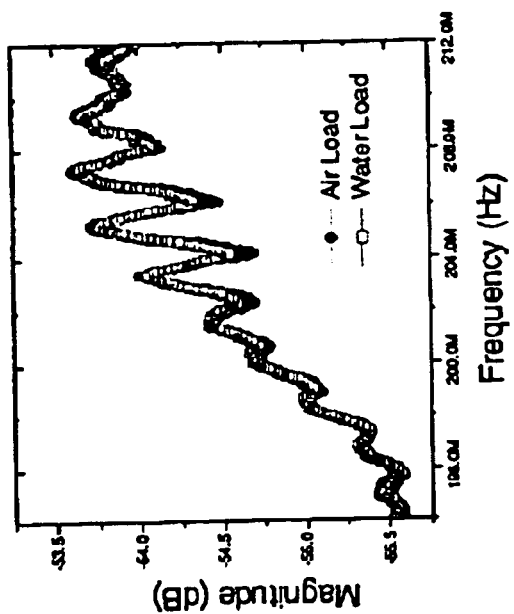
FIG. 14b shows an analysis demonstrating the liquid attenuation of a dual mode AlN/Sapphire acoustic wave sensor operating in STW mode.
Figure 14A:
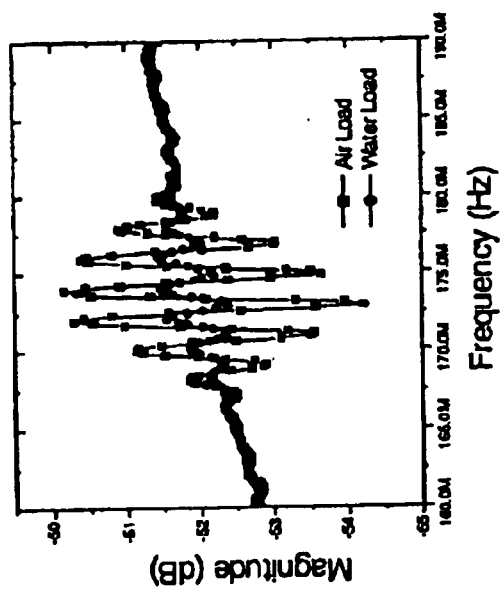
FIG. 14a shows an analysis demonstrating the liquid attenuation of a dual mode AlN/Sapphire acoustic wave sensor operating in a SAW mode.

FIGS. 14*a* and 14*b* show an analysis demonstrating the liquid attenuation effect on AlN/Sapphire acoustic sensors when placed in water. FIG. 14*a* shows the liquid attenuation of an acoustic wave sensor operating in a SAW mode, and FIG. 14*b* shows the liquid attenuation of an acoustic wave sensor operating in STW mode. As shown in FIG. 14*a*, the amplitude of the output signal is reduced by almost 80%. It is believed that this reduction is due to the movement direction of the particles, which is perpendicular to the surface of the sensor in the SAW mode. In FIG. 14*b*, the output signal is almost unchanged for the STW mode when the sensor is also put into a water load since particles move parallelly in the STW mode. It is therefore believed that AlN-based acoustic wave sensors operating in the STW mode should be suitable for use in chemical and biological sensors.

The AlN-based acoustic wave biosensor arrangements may be used for real time sensing and for quantifying the levels of *E. Coli* bacteria. Many monoclonal antibodies with high affinity and specificity for *E. Coli* may be available from commercial sources as well as the American Type Culture Collection (ATCC). One of these antibodies, the ATCC HB-8178 antibody, may bind specifically with the *E. Coli* pilus. This antibody may possess high specificity for pili associated antigen proteins, so that binding with other proteins present in water samples should be minimal or at least reduced.

The monoclonal antibody produced by the hybridoma cell line HB-8178 may be a human lymphocyte antibody specific for *E. Coli* pilus coat proteins. It may bind with high specificity and affinity to the *E. Coli* pilus. The hybridoma cell line producing this (ATCC HB-8178) may be available for a nominal fee from the American Type Culture Collection. The anti-*E. Coli* immunoglobulin is purified using a Protein A sepharose column and stored in phosphate buffered saline solute. It is prepared for conjugation by microcentrifugation in a mini-prep protein A sepharose column and then resuspended in appropriate buffer for the coupling chemistry. FIG. 15 shows several coupling chemistries that may be used for binding the monoclonal antibody to the sensor chip surface. Such coupling chemistries may provide the highest loading of the IgG monoclonal antibody per unit area on the chip. The surface of the AlN-based acoustic wave biosensor device may be terminated with gold, nitrogen or oxygen. The SANPA bifunctional linkers use a NHS ester link to the free amine on the monoclonal antibody. The photo-activated linkage of the oxide group is non-specific, and should be important to bind to adjacent nitrogen or oxygen on the aluminum on the AlN surface.

It may also important to optimize the chemical linking of the antibody, as well as the loading density. Independent fluorescence assays of the antibody density on the chip may be done using fluorescence labeled anti-IgG. The chip may be incubated in phosphate buffered saline with fluorescein labeled anti-IgG, and may then be washed with a buffer solution of increasing ionic strength to dislodge unbound antibody. The chip may then be scanned using a Perkin Elmer LS50B fluorescence spectrophotometer, and the bound antibody density may be calculated using FL-Winlab software, which may also calculate various parameters (such as, for example, the statistical variability observed in the surface loading between regions on the chip sample surface). This technique may be used to determine which of the coupling chemistries yields the best loading of antibodies.

Biologically detecting of environmental contaminants may require detecting of smaller molecular weight molecules relative to the larger protein molecules that monoclonal antibodies Micromass may be directed against. Monoclonal antibodies may be available against relatively few chemicals of environmental interest. A rabbit monoclonal antibody against dinitrophenol (DNP), which may be available from Biodesign International, may have a high specificity and affinity to dinitrophenol and may be provided in a neat serum with a dilution point of 1:32,000. Dinitrophenol may be comparable in size to the aromatic and ring containing pesticides that may be of interest for remote sensing in the environment. Also, Dinitrophenol may serve as the classic small molecule used as a hapten for evaluating the generation of monoclonal antibodies against such small molecules. FIG. 16 shows that it may be useful as an analyte for showing the performance of the biosensor arrangement 100b against the relatively smaller environmental contaminants that may be the target of a smart biosensor device.

The same coupling chemistry methods described above may be used for coupling the anti-DNP monoclonal antibody to the biosensor surface. Quantitation of the bound anti-DNP monoclonal antibody may be performed with the same fluorescein labeled techniques described above except that fluorescein labeled anti-rabbit IgG may be used. Once it is determined that the biosensor chip is adequately loaded with the anti-DNP antibody, the biosensor arrangement may be tested for the current generated against a range of analyte solution concentrations from 0.1 ppm to 200 ppm. The quantity of DNP bound analyte on the biosensor surface may be related to the generated current, and compared to the biosensor response against the larger whole cell $E.$ $Coli$ detection system described above.

The same coupling chemistry methods described above may be used for coupling the anti-toluene monoclonal antibody to the biosensor surface. Quantitation of the bound anti-toluene monoclonal antibody may be performed with exactly the same anti-rabbit IgG fluorescein technique as for the anti-DNP antibody, since the toluene recognizing monoclonal antibody is a rabbit IgG. Once it is determined that the biosensor arrangement is adequately loaded with the anti-toluene antibody, the biosensor arrangement may be tested for the current generated against a similar range of analyte solution. In this case actual groundwater samples may be obtained and spiked with toluene over the 0.1 ppm to 200 ppm concentration to be examined. This may be important for demonstrating that the background ions present in groundwater such as iron, sodium, manganese, etc. do not affect the biosensor response.

Current generated per analyte molecule bound to the biosensor surface may be compared for these relatively small environmental analytes with molecular weights typically ranging from 100 to 400 daltons to the response obtained from experiments with $E.$ $Coli$ cells. Since $E.$ $Coli$ cells may have an average hydrodynamic radius on the order of 1 μm, there may be differences in the mass and size of these two types of environmental contaminants to be examined. Analyzing the differences in the biosensor response may be useful for improving the chemistry and spatial properties of the biosensor arrangement to enhance its performance against the analyte of interest.

It is believed that monoclonal antibodies have not been used as detection agents for the environmental contaminants of interest because of the relative by small size of these organic chemical analytes. Molecules of molecular weight less than 500 daltons may have to be conjugated with a larger carrier protein, such as albumin, and presented to the host with an adjuvant to stimulate the host animal to develop a clonal population of antibody producing B-lymphocytes which recognize the hapten (analyte) molecule. This process, in which an animal host system is used for the production of the hybridoma cell line and subsequent Elisa screening techniques may be used to identify the B-lymphocyte clone for fusion with the myoblast cell line to produce the hybridoma cell line of interest, may be expensive and time consuming (taking 1 to 2 years, for example). These monoclonal antibody products may be proprietary and the expense of developing these types of biological agents for environmental applications may be prohibitive. Hence, the power of monoclonal antibody specificity and binding characteristics may not apply to the environmental area. The advent of molecular biology tools that allow for direct combinatorial rearrangement of the heavy and light chain hypervariable regions of the antibody recognition sites may provide for the bypassing of the animal host, and the production and screening of monoclonal antibodies with greater efficiency and lower cost.

One method uses DNA from a pre-B lymphocyte which may have a large pool of potential B-lymphocyte specificity, since the pre-B cell DNA has not yet been processed to the form of the mature monoclonal antibody producing B-lymphocyte, so as to maintain its molecular diversity. This DNA may be amplified by polymerase chain reaction (PCR) using primers upstream and downstream to the heavy (H) and (L) chain regions. The resulting DNA segments may be linked with "linker sequences" using standard PCR technology available in kit form from Perkin Elmer Scientific. These DNA sequences may be ligated to phamid sequences in the PIII or PVIII gene and the linear phage (such as, for example, T4) may be used to reinfect the host bacteria ($E.$ $Coli$) which may result in expression of the $V_H$ and $V_L$ genes which are the peptide regions of the monoclonal antibody that encode the analyte specificity sought in these studies. The $E.$ $Coli$ cells may be subjected to a "biopanning" procedure where the $E.$ $Coli$ cells may be plated out and cultured to express the monoclonal antibody heavy and light chain encoding proteins on their cell surface with the phage proteins (see, for example, L. J. Partridge, "Production of Catalytic Antibodies using Combinatorial Libraries", Biochem Soc Trans 21(4), 1096 (1993) and P. K. Kuo, G. W. Auner, and W. U. Huse, L. Sastry, S. A. Kang, M. Alting-Mees, S. J. Benkovic, and R. A. Lerner, "Generation of a Large Combinatorial Library of the Immunoglobulin Repertoire in Phage Lambda", Science, 246, 1275 (1989)).

The petri dish may be blotted with cellulose acetate filter paper, and may be washed with a phosphate buffer solution containing the analyte of interest. After extensive blank washes in phosphate buffered saline, the cellulose filter papers may be extracted into hexane and the hexane extract may be analyzed on the gas chromatograph for the analytes of interest, as referred to in FIG. 16. Negative controls may consist of cellulose filters that have been blotted against non-infected E. Coli cultures, which have also been subjected to "biopanning" with the analyte solution. This screening technique may result in the isolation of E. Coli "clones" that produce the binding fragments ($V_H$ and $V_L$) and present them in their cell walls. These bacterial cell walls may then be fragmented and isolated by density gradient centrifugation and immobilized on the biosensor arrangement using the polymer monolayer with amine coupling functional group technique, as referred to at FIG. 15.

It is believed that this combinatorial for producing monoclonal antibody structural fragments that bind analytes of environmental interest may expand the range of organic contaminant species that the biosensor may be sensed by, and that this repertoire of biological diversity may increase the range of applications of biosensors for remote by sensing environmental pollutants.

The exemplary emodiments and/or exemplary methods may also provide several benefits in the area of wireless networking of low-powered microsensors, which may be suitable for numerous applications. The sensor devices may be implemented by computer simulation in a Materials and Device Simulation Laboratory and/or an laboratory. In particular, VLSI implementation may be done in a Smart Sensor and Integrated Microsystem (SSIM) laboratory using various design, simulation, and implementation software (such as, for example, Mentor Graphics Software). The specification may then be sent through the MOSIS system for fabrication, followed by hybridizing the sensor and integrated circuit in the EMIT laboratory. The MOSIS Service may be a low-cost prototyping and small volume production service for developing custom and semi-custom VLSI circuit arrangements.

Available technologies may include digital CMOS, mixed signal CMOS, GaAs, and multi-chip module (MCM) fabrication. In the case of acoustic arrays on silicon substrates, both hybrid chip technology and direct low temperature growth of AlN structures on the VLSI chip may be used. For the case of sensor arrays on sapphire chips, hybridizing techniques may be used. The VLSI circuitry may be developed and fabricated using MOSIS with a surface mounting section for sensor chip integration. In an exemplary embodiment, VLSI circuitry may be integrated with an r.f. transceiver circuit arrangement. The transceiver circuit arrangement may be a wireless transceiver monolith (which may be available commercially) that may communicate via cell phone transmission to transfer data from the biosensor arrangement.

The sensor arrangement may be a bacteria-detecting arrangement with associated VLSI analog and/or digital circuitry, which may be made in the SSIM laboratory. The device may be hybrid to a commercial controller and transceiver unit for communication of data. The sensing system may detect small concentrations of bacterial pollution and transmit the data at predetermined time intervals. The sensing system may also include a microsensor array on a chip for detecting of multiple pollutants. Shear acoustic wave sensors and the characterization of the device responses may be use to provide special application specific integrated circuits, including electronics communications. The VLSI chip may be hybridized with the sensor, and with a control and transceiver arrangement, such as, for example, Monolithic IC Inc.

Figure 17:
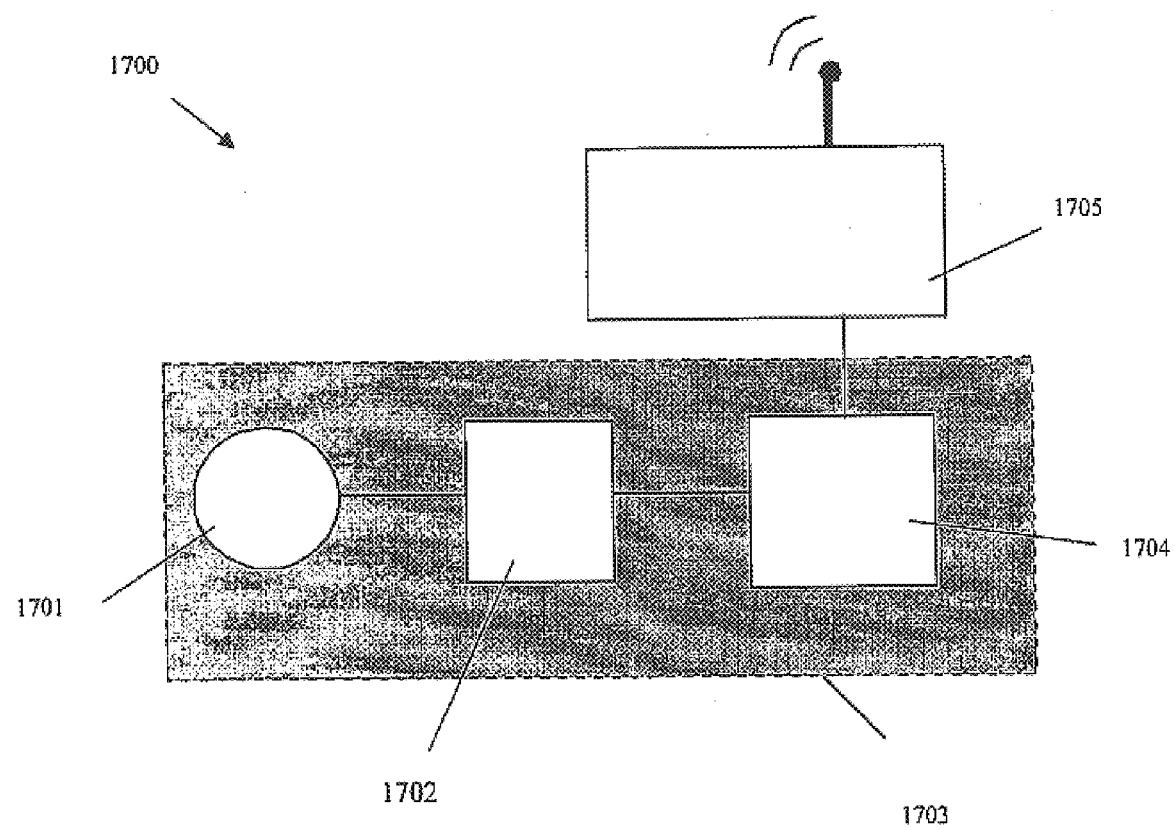
FIG. 17 shows a block diagram of a sensor system with integrated electronics.

FIG. 17 shows a block diagram of a sensor system 1700 with integrated electronics. The sensor system 1700 includes an acoustic wave biosensor 1701, an analog interface 1702, and a digital interface 1704 in a sealed unit 1703. The sensor system 1701 further includes an encapsulated transceiver arrangement 1705, which may be available from Monolithic Devices Inc.

The exemplary embodiments and/or exemplary methods involve an integrated hardware and software approach for providing wireless networked microsensors, which may be energy-efficient, fault-tolerant, and scalable. In addition, they may support continuous operation and provide diagnostic capabilities. In this regard, severe limits on the computational and memory capabilities of such smart sensors may place constraints on the communication protocol. Accordingly, an external communication device, which may be contained in a sealed floating unit, may be used to provide additional resources that may be required for protocol-compliant communication, including increased range and bandwidth. Software to display the data and/or message contents may be provided to validate the network protocols and the sensor communication. The wireless network protocols should provide energy-efficient communication between the sensor or sensor array and an external base station. Image analysis and recognition software may also be used.

An exemplary embodiment may include the following key features: (1) resiliency to component failures, including failure of embedded sensors and wireless link failure due to interference; (2) communication protocols should support expansion to multiple sensor arrays; and (3) the sensor microsystem should be operable for many hours per day and/or for years.

The exemplary embodiment may also be optimized to meet particular capacity, coverage, reliability, and maintainability requirements. For example, considering the relatively small physical size of the area that the biosensor arrangements, a point-to-point network may be use in which an external transmitting device communicates directly with each of the smart sensor arrays. Such an arrangement may also simplify the networking protocol stack by eliminating the need for multi-hop routing between smart sensors.

Bandwidth allocation to channels may be done using time division, frequency division, code division, and/or space division methods. For example, code division (or spread spectrum methods) may be used since such methods should be robust against narrow band interference. As another example, frequency hopping spread spectrum (FHSS) may be used since it may be less complex to implement than direct sequence spread spectrum (DSSS). An optimum set of hopping sequences may be determined depending on the density and relative placement of the smart sensor arrays.

For the environmental sensor array application, the mechanisms to share a radio channel may include TDMA and CDMA. The selection may depend on the nature of the traffic pattern, tolerable levels of multi-user interference, power requirements, desired spectral efficiency, and the complexity of the resulting system. Periodic communications in the application may suggest that TDMA is an appropriate choice. Furthermore, reservation-based TDMA with a centralized controller may permit broadcasting of the communication schedule, which may be used by a biosensor arrangement to determine how long to remain active in a TDMA cycle. Such techniques may be used to power down the biosensor arrangement when they do not need to be active. As such, this power-saving optimization may reduce overall system power consumption.

The processing and communication hardware and software may be highly integrated, and optimizations across all layers of the system may be provided to minimize energy dissipation. For instance, energy dissipation may be optimized using energy conscious network protocols for collaborative sensing and information distribution, smart system partitioning based on communication and computation costs, low-power electronics, and/or using energy "harvesting" methods.

Reliability may also be provided for both the hardware and software. This may involve, for example, identifying which of the embedded components has failed. Since it may be difficult and expensive to frequently replace sensors, redundancy may be built in to better ensure the operational longevity of the sensor arrays. The level of redundancy may depend upon the failure rate of each individual component. Furthermore, diagnostic mechanisms may be used to identify the faulty components and to reconfigure the system to overcome the faults. The external base station may periodically initiate diagnostic checks on each of the sensor systems. An error correction mechanism, such as ARQ and FEC, may be selected based on the reliability requirements. As such, the protocol mechanism may be simple and power-efficient (such as, for example, the stop-and-wait ARQ protocol).

The characterization of a device response may be obtained from a device frequency response spectrum, which may provide information regarding the device performance such as insertion loss, oscillation frequency, and/or bandwidth. Accordingly, acoustic wave sensor arrangements may be characterized routinely in this manner.

Figure 18:
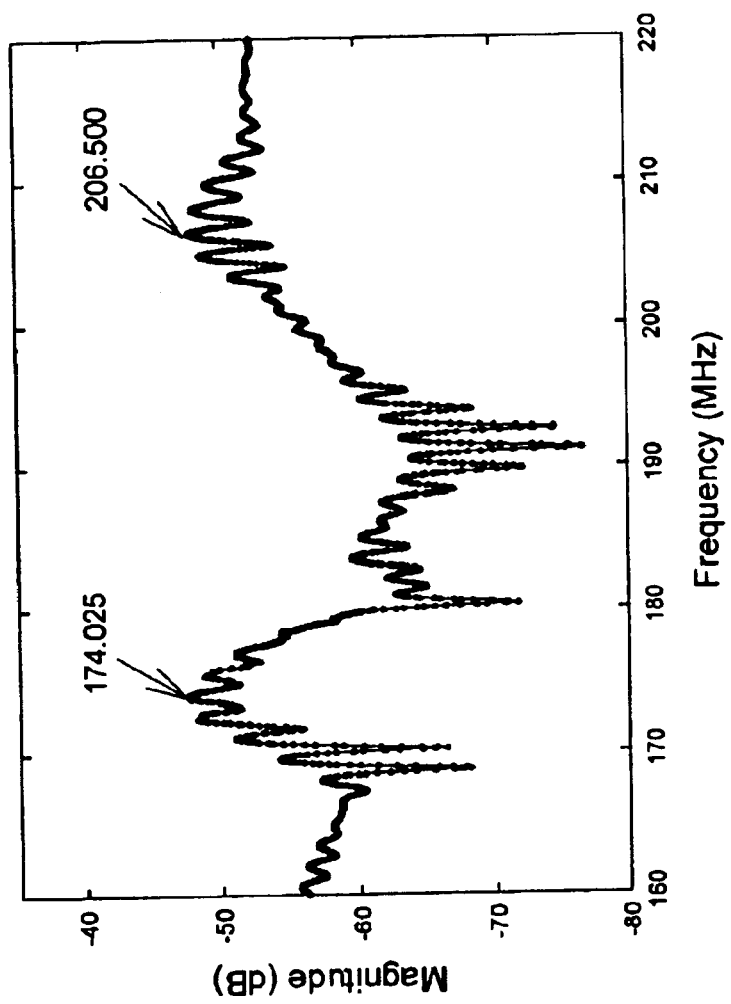
FIG. 18 shows a frequency response of a dual mode AlN/Sapphire acoustic wave biosensor device with central energy trapping gratings for both SAW and STW modes.

FIG. 18 shows a frequency response of a dual mode device with central energy trapping gratings for both SAW and STW modes. As shown in FIG. 18, the dual mode device may result in a center frequency of SAW at 174.025 MHz and STW at 206.500 MHz. For devices without central gratings, only a SAW mode may be provided.

The phase velocity of an acoustic wave may be determined using the equation in which $f_o$ is the center frequency and $\lambda$ is acoustic wavelength. For a value of 32 µm, the calculated phase velocity is 5569 m/s for the SAW mode and 6608 m/s for the STW mode. The STW velocity of the dual mode device may be higher when compared to 6040±80 m/s. Variations may be due to the nature and thickness of the epitaxial layers films.

According to FIG. 18, the insertion loss at the center frequency of SAW mode is about 15 dB less than that of the background signal. The STW mode also yields about an 8 dB dynamic range. Once the attenuation introduced by the immobilization layer is beyond 18 dB for the SAW mode or 8 dB for the STW mode, the signal may be covered by background noise and the biosensor arrangement may no longer operate, as a practical matter.

Figure 19B:
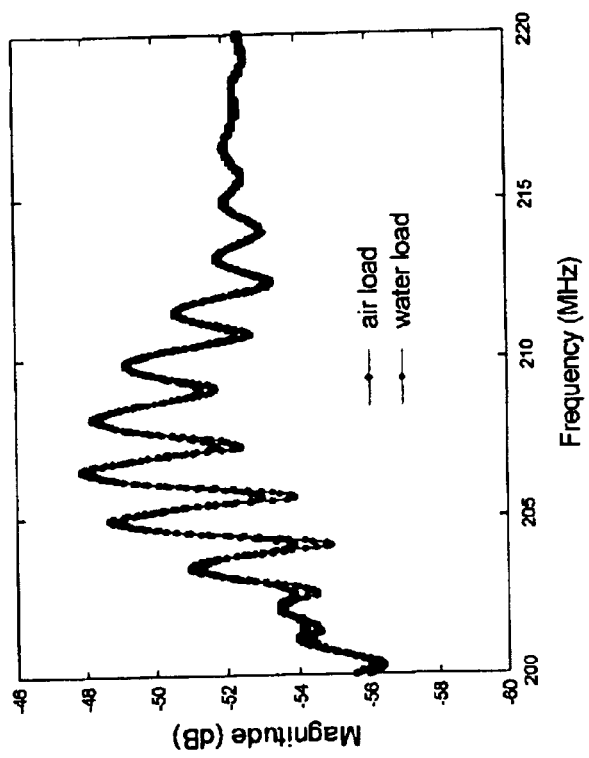
FIG. 19b shows a frequency response of a dual mode AlN/Sapphire acoustic wave biosensor operating in a STW mode under a water load to show the effects of liquid attenuation.
Figure 19A:
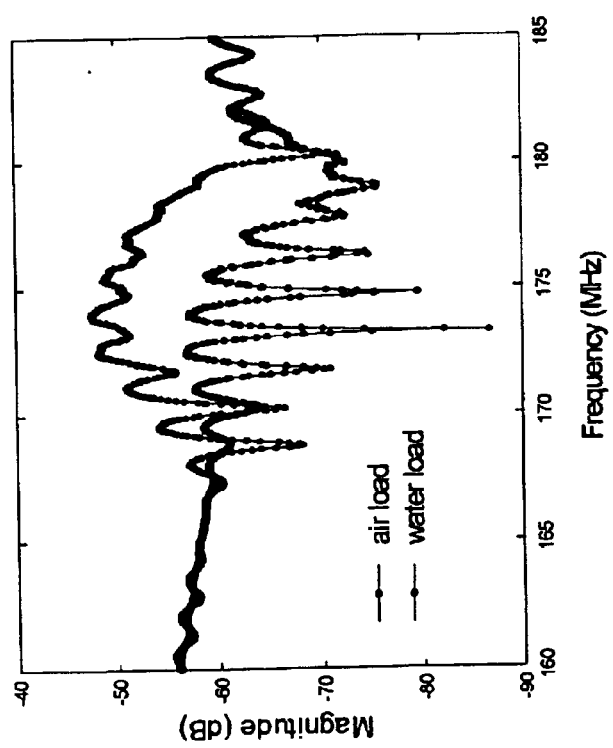
FIG. 19a shows a frequency response of a dual mode AlN/Sapphire acoustic wave biosensor operating in a SAW mode under a water load to show the effects of liquid attenuation.

FIGS. 19a and 19b show the frequency response of a dual mode AlN/C-Sapphire acoustic wave biosensor device under a water load so as to demonstrate the effects of liquid attenuation. FIG. 19a shows the effect of liquid attenuation of the sensor operating in a SAW mode, and FIG. 19b shows the effect of liquid attenuation of the sensor operating in a STW mode. Liquid attenuation was provided by putting 5 µl tap water on the region between the IDTs. The SAW mode operation may be severely attenuated because the perpendicular motion of particles to the device surface may easily radiate energy in a liquid environment. The amplitude for the STW mode, however, is about the same due to its shear horizontal polarization characteristic.

Figure 20:
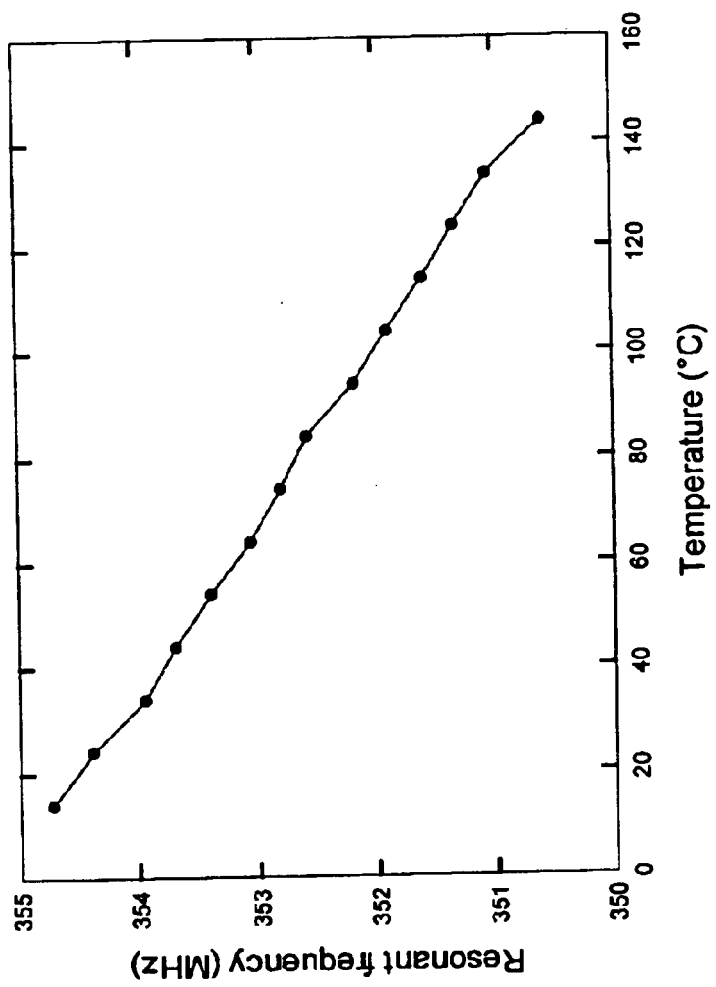
FIG. 20 shows a temperature sensitivity characteristic of an AlN-based acoustic wave arrangement.

FIG. 20 shows the temperature sensitivity characteristic of an AlN-based acoustic wave arrangement. In particular, the arrangement is a SAW resonator having a 16 µm wavelength on a thermal-electric stage. As shown in FIG. 20, there is a near linear temperature coefficient of about 90 PPM/° C. This near linear temperature coefficient of AlN-based acoustic sensors may eliminate the need for providing additional temperature compensation or stabilizing methods that may be required by acoustic wave sensors that do not use AlN or other wide bandgap materials.

Antibody immobilization may be important to successfully providing liquid-phase biological detection. The chemical linker may need to show good affinity to both AlN and antibody being immobilized. A specific compound, -(p-maleimidophenyl)isocyanate (PMPI) may be used due to its chemical properties. A SAW mode arrangement with a 32 µm wavelength is provided for a PMPI linker mass loading experiment. The PMPI linker is first dissolved in a buffer liquid, and is then applied on the center area of the arrangement by a micro-syringe. In particular, the applied volume is approximately 2 µl, and the PMPI linker is applied by micro-syringe onto the center region between IDTs of the device.

Figure 21:
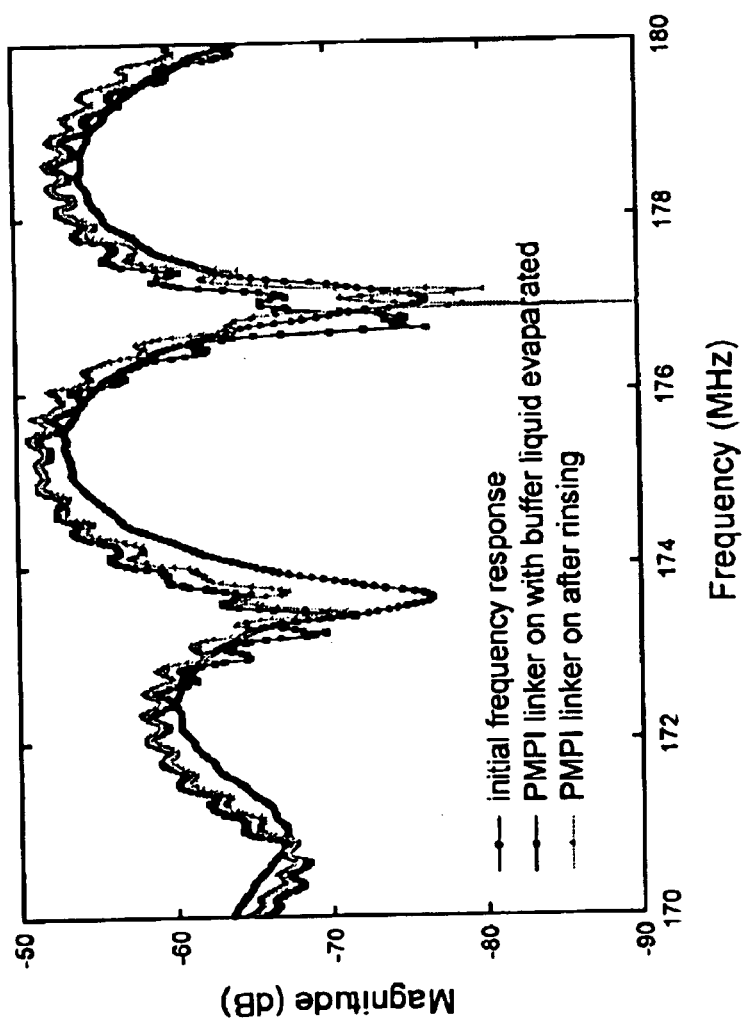
FIG. 21 shows a mass loading effect using a p-maleimidophenyl isocyanate (PMPI) linker.

FIG. 21 shows a mass loading effect using a PMPI linker. Three frequency response measurements are shown: an initial frequency response measurement; a second measurement taken overnight after applying the PMPI linker so that the buffer liquid has evaporated; and a last measurement taken after a de-ionized water rinsing. A frequency shift $\Delta f$, relative to the initial response, may be observed in both cases with the PMPI linker on both before and after the de-ionized water rinse. It is believed that this indicates that the PMPI linker may still exist after the de-ionized water rinse.

$\Delta f_1 = 173.425 - 173.631 = -0.206$ MHz (between second and initial), and $\Delta f_2 = 173.481 - 173.631 = -0.150$ MHz (between last and initial).

Figure 22:
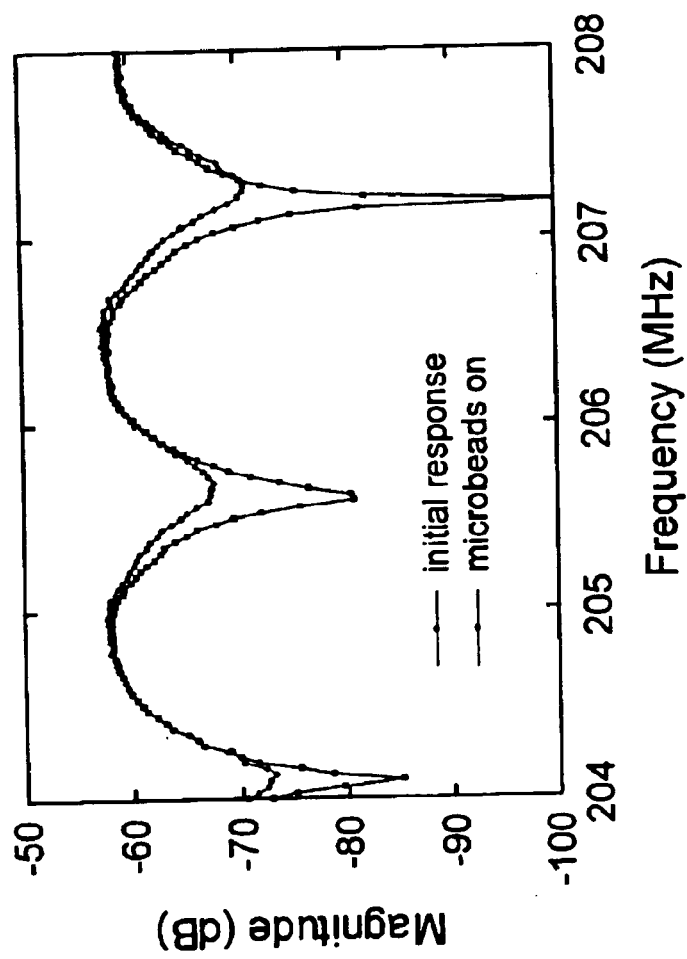
FIG. 22 shows a mass loading effect using magnetic micro-beads that were applied onto a dual mode AlN/Sapphire acoustic wave biosensor device by a micro-syringe.

According to FIG. 21, there is no clear change in magnitude, which indicates that the nature of the perturbation may be largely elastic. As a result, that PMPI linker's elastic modulus may be considered small enough for modulus effects to be neglected. Small notches on the waveforms after the PMPI linker is applied may be due to the non-uniformity of the PMPI linker layer. An alternative immobilization method may be used. For example, FIG. 22 shows a mass loading effect using magnetic micro-beads that were applied onto a dual mode device by a Micro-syringe. To demonstrate the liquid sensing potential of the arrangement, it operates in the STW mode. As shown in FIG. 22, the application of micro-beads results in a negative frequency shift of 0.094 MHz (which should correspond with the theory of the mass perturbation mechanism).

In addition to measuring the frequency response of acoustic wave (AW) sensors, other measuring techniques may be used. Although a frequency response spectrum may be a valuable AW sensor characterization tool, there may be reasons not to use it as a routine way to monitor the real time response of an AW sensor. First, the amount of time to obtain a frequency response spectrum may vary from one to several minutes depending on the frequency resolution and noise level desired. Second, frequency shift information may only be obtainable by comparing among different measurements, rather than through direct observation. Finally, the accuracy in terms of the peek frequency may be limited by the resolution of the network analyzer.

Several available measurement techniques may be used. In this regard, FIG. 23 shows a propagation measurement arrangement 2300. A signal generator 2301 provides a signal of fixed frequency and amplitude to the input IDTs 2304. A frequency counter 2302 then monitors the output frequency and imports it to a computer 2303, which calculates the frequency shift. Changes in surface attached mass are proportional to the changes in frequency. Thus, a quantitative relation may be determined theoretically.

Still further, FIG. 24 shows an oscillator loop based measurement arrangement 2400. The frequency counter 2302 of FIG. 23 is replaced by a vector voltmeter across the input and output IDTs 2408 using a power splitter 2407 so that both amplitude changes and phase (frequency) shift between the IDTs 2408 may be obtained. The AW device 2408 may be considered a feedback path for the amplifier (AMP) 2401. To reach stable operation, the round trip phase shift in the closed loop should equal the integer multiple of $2\pi$, and the gain of the chosen AMP 2401 should be greater than or at least equal to the insertion loss of the device 2408 at the operating frequency. An automatic gain control 2403 circuit may be used with the AMP 2401 to maintain the oscillation amplitude and a phase shifter 2404 may be used to better ensure the required phase compensation. A bandpass filter 2402 excludes any harmonics generated by the AMP 2401, so as to avoid false input to frequency counter 2406, and associated computer 2405. In contrast to the oscillator loop based measurement arrangement, propagation measurements may not provide the same sensitivity but may not be subject to mode hopping associated with an oscillator circuit under certain circumstances.

The arrangements of FIGS. 23 and 24 may be constructed using line-powered discrete instruments, DC-powered components on printed circuit board with surface-mounting devices, or integrated circuit technology to corporate each of the components on a single wafer.

Figure 25:
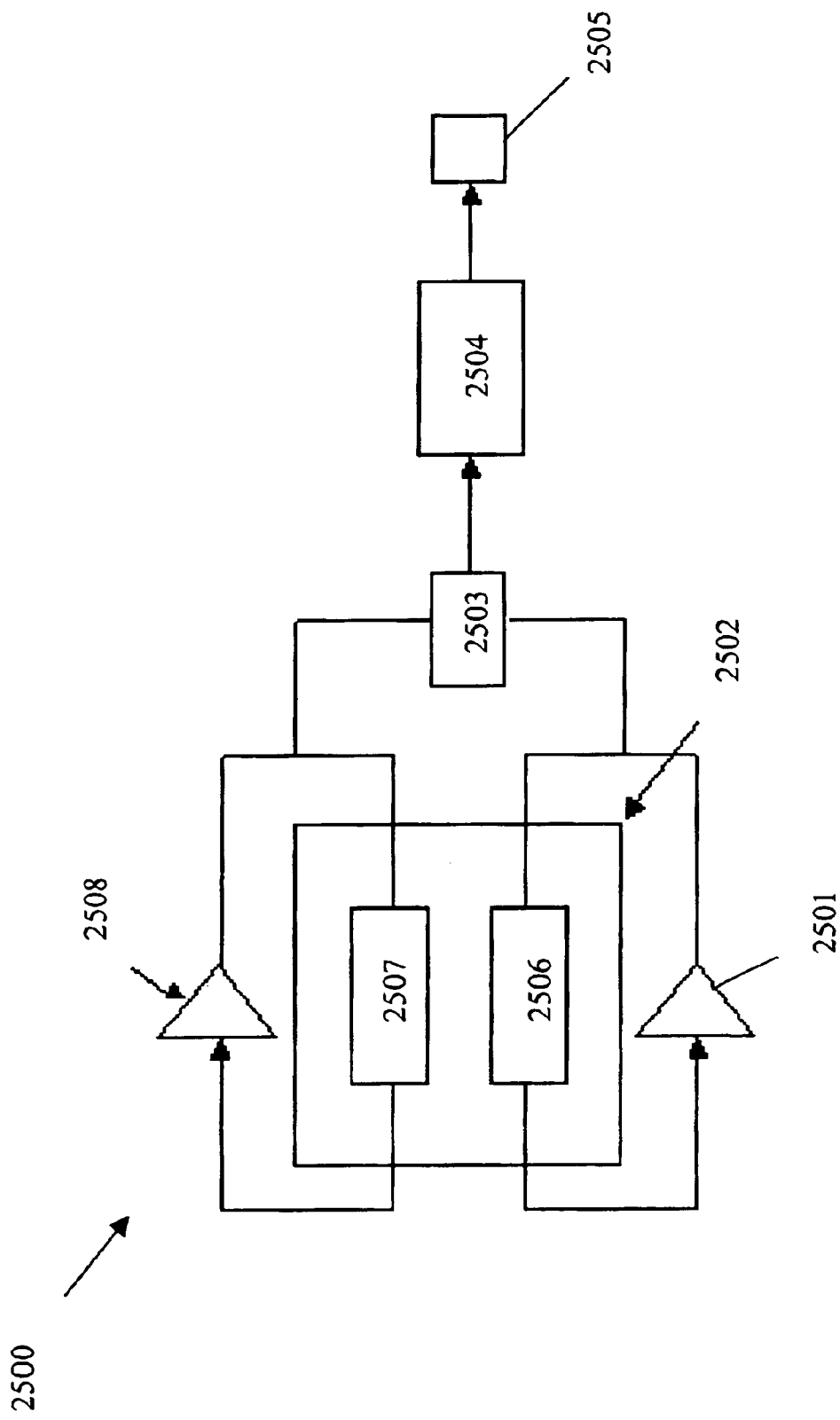
FIG. 25 shows a differential configuration setup to perform a differential-based measurement method.

FIG. 25 shows a differential configuration setup 2500 to perform a differential-based measurement technique. The differential configuration setup 2500 includes an amplifier 2508 coupled to an AW sensor 2507, an amplifier 2501 coupled to a reference AW sensor 2506, a mixer 2503, a lowpass filter 2504, and an outwit 2505. The differential configuration setup 2500 may be used to compensate for environmental influences on AW sensors 2506, 2507, such as temperature, humidity, and pressure variation. It may be assumed that the two sensors 2506, 2507 in the same environment 2502 are the same, except that the reference sensor 2506 is not in contact with the analyte to be detected. An intrinsic problem, however, may be that two exact identical sensors 2506, 2507 may require very high quality control during the fabrication process. In reality, one sensor may need to ensure that the environmental effect is much greater than the influence arising from differences between the two sensors 2506, 2507.

What is claimed is:

1. An acoustic wave sensor to detect an analyte, comprising:
 a piezoelectric material including a wide bandgap semiconductor material grown using plasma source molecular beam epitaxy;
 a micro-machined arrangement having a resonating frequency; and
 an immobilization layer traversing the micro-machined arrangement, the layer containing a binding site to allow a target structure of the analyte to bind to the micro-machined arrangement so as to chance the resonating frequency,
 wherein the immobilization layer includes a chemical linker and wherein the chemical linker is p-maleimidophenyl isocyanate.

2. An acoustic wave sensor to detect an analyte, comprising:
 a piezoelectric material including a wide bandgap semiconductor material grown using plasma source molecular beam epitaxy;
 a micro-machined arrangement having a resonating frequency;
 an immobilization layer traversing the micro-machined arrangement, the layer containing a binding site to allow a target structure of the analyte to bind to the micro-machined arrangement so as to change the resonating frequency;
 a laser diode arrangement capable of high frequency modulation to generate a pulsed laser light;
 a waveguide arrangement to transport the pulsed laser light; and
 a carbon implanted region to receive the pulsed laser light and to provide a bulk wave to the micro-machined arrangement.

3. The acoustic wave sensor of claim 2, wherein the waveguide arrangement is fabricated using a wide bandgap semiconductor material using plasma source molecular beam epitaxy.

4. The acoustic wave sensor of claim 3, wherein the waveguide arrangement includes aluminum nitride.

5. The acoustic wave sensor of claim 2, further comprising an array of waveguide arrangements.

6. The acoustic wave sensor of claim 2, wherein the sensor includes a photonic waveguide coupling to reduce noise and cross-talk at a high frequency.

7. An acoustic wave sensor to detect an analyte, comprising:
 a piezoelectric material including a wide bandgap semiconductor material grown using plasma source molecular beam epitaxy;
 a micro-machined arrangement having a resonating frequency; and
 an immobilization layer traversing the micro-machined arrangement, the layer containing a binding site to allow a target structure of the analyte to bind to the micro-machined arrangement so as to change the resonating frequency,
 wherein the sensor is operable to detect 5 molecules of 100,000 daltons.

8. An acoustic wave sensor to detect an analyte, comprising:
 a piezoelectric material including a wide bandgap semiconductor material grown using plasma source molecular beam epitaxy;

a micro-machined arrangement having a resonating frequency; and an immobilization layer traversing the micro-machined arrangement, the layer containing a binding site to allow a target structure of the analyte to bind to the micro-machined arrangement so as to change the resonating frequency, wherein the sensor is operable to detect a binding of a monolayer of oxygen to less than 1% of a 100 µm×100 µm surface area of the sensor.

9. A method for operating an acoustic wave sensor, comprising:

generating an acoustic wave;

directing the acoustic wave to transverse a micro-machined arrangement;

detecting a resonating frequency of the micro-machined arrangement;

determining a presence of an analyte based on the detected resonating frequency, wherein the analyte contains a target structure that binds to an immobilization layer of the micro-machined arrangement;

providing a laser light from a laser diode via a waveguide arrangement; and receiving the laser light in a carbon-implanted region.

10. An acoustic wave sensor to detect an analyte, comprising:

a piezoelectric material including a wide bandgap semiconductor material grown using plasma source molecular beam epitaxy;

a micro-machined arrangement having a resonating frequency; and an immobilization layer traversing the micro-machined arrangement, the layer containing a binding site to allow a target structure of the analyte to bind to the micro-machined arrangement so as to change the resonating frequency, wherein:

the micro-machined arrangement includes a wide bandgap semiconductor material;

the sensor is operable in a surface acoustic mode;

the sensor is operable in a surface transverse mode;

the sensor is operable in a liquid medium and maintains a high sensitivity without a severe attenuation;

the immobilization layer includes a chemical linker; and the chemical linker is p-maleimidophenyl isocyanate.

* * * * *